(12) United States Patent
Chen et al.

(10) Patent No.: US 7,805,177 B2
(45) Date of Patent: Sep. 28, 2010

(54) METHOD FOR DETERMINING THE RISK OF RUPTURE OF A BLOOD VESSEL

(75) Inventors: David T. Chen, Wrentham, MA (US); Jeff Dwyer, Dublin, NH (US); Mark F. Fillinger, Hanover, NH (US); Steven P. Marra, Lebanon, NH (US); M. Weston Chapman, Hanover, NH (US)

(73) Assignee: M2S, Inc., West Lebanon, NH (US)

( * ) Notice: Subject to any disclaimer, the term of this patent is extended or adjusted under 35 U.S.C. 154(b) by 1107 days.

(21) Appl. No.: 11/159,595

(22) Filed: Jun. 23, 2005

(65) Prior Publication Data

US 2006/0100502 A1 May 11, 2006

Related U.S. Application Data

(60) Provisional application No. 60/582,128, filed on Jun. 23, 2004.

(51) Int. Cl.
 *A61N 1/362* (2006.01)
(52) U.S. Cl. ..................... 600/407; 600/419
(58) Field of Classification Search .......... 600/407
 See application file for complete search history.

(56) References Cited

U.S. PATENT DOCUMENTS

| 4,945,478 | A | 7/1990 | Merickel et al. |
| 5,731,817 | A | 3/1998 | Hahs, Jr. et al. |
| 5,987,236 | A | 11/1999 | Yoneda |
| 6,226,405 | B1 * | 5/2001 | Furuhata et al. .......... 382/197 |
| 6,447,454 | B1 | 9/2002 | Chenal et al. |
| 6,456,289 | B1 | 9/2002 | O'Brien et al. |
| 6,511,426 | B1 | 1/2003 | Hossack et al. |
| 6,523,416 | B2 | 2/2003 | Takagi et al. |
| 6,538,634 | B1 * | 3/2003 | Chui et al. .......... 345/156 |
| 6,895,383 | B2 | 5/2005 | Heinrich |

(Continued)

FOREIGN PATENT DOCUMENTS

WO  WO 02/29758  4/2002

(Continued)

OTHER PUBLICATIONS

Di Martino, E.S. et al., Fluid-structure interaction within realistic three-dimensional models of aneurysmatic aorta as a guidance to assess the risk of rupture of the aneurysm, Medical Engineering & Physics, 2001, 647-655, 23.

(Continued)

*Primary Examiner*—Long V Le
*Assistant Examiner*—Hien Nguyen
(74) *Attorney, Agent, or Firm*—Paradiscio & Paradiscio

(57) ABSTRACT

There is provided a method and apparatus for determining the risk of rupture of a blood vessel using a set of 2-D slice images obtained by scanning the blood vessel. The invention includes elements and steps for generating a mesh model of the blood vessel using the set of 2-D slice images, conducting finite element stress analysis on the mesh model to calculate the level of stress on different locations on the mesh model and determining the risk of rupture of the blood vessel based on the calculated levels of stress on different locations on the mesh model.

34 Claims, 35 Drawing Sheets

U.S. PATENT DOCUMENTS

| | | | |
|---|---|---|---|
| 6,940,505 B1* | 9/2005 | Savine et al. | 345/423 |
| 7,158,692 B2* | 1/2007 | Chalana et al. | 382/294 |
| 7,353,214 B2 | 4/2008 | Yamanishi et al. | |
| 2002/0033454 A1* | 3/2002 | Cheng et al. | 250/339.12 |
| 2002/0184245 A1* | 12/2002 | MacPherson | 707/202 |
| 2003/0097068 A1* | 5/2003 | Hossack et al. | 600/443 |
| 2004/0009459 A1* | 1/2004 | Anderson et al. | 434/262 |
| 2005/0004467 A1* | 1/2005 | Shiina et al. | 600/449 |

FOREIGN PATENT DOCUMENTS

| | | |
|---|---|---|
| WO | WO 02/97735 | 12/2002 |

OTHER PUBLICATIONS

Raghavan, M.L. et al., Wall stress distribution on three-dimensionally reconstructed models of human abdominal aortic aneurysm, Journal of Vascular Surgery, Apr. 1, 2000, 760-768, vol. 31, No. 4.

* cited by examiner

CUMULATIVE SUM TABLE (LENGTHS)

| INDEX | SUM OF LENGTHS |
|---|---|
| $c_0$ | 0 |
| $c_1$ | 1.5 |
| $c_2$ | 2 |
| $c_3$ | 4 |
| ⋮ | ⋮ |

CUMULATIVE SUM TABLE (VOLUME)

| INDEX | SUM OF VOLUMES |
|-------|----------------|
| $c_0$ | 1.5 |
| $c_1$ | 4 |
| $c_2$ | 5.2 |
| $c_3$ | 6 |
| ⋮ | ⋮ |

MMS Reconstruction of an actual abdominal aortic aneurysm. Regions where the blood is flowing are in red (dark gray in this black and white figure), regions of thrombus and plaque formation are in yellow (light gray), and regions of calcium are in white.

Screen capture of MMS reconstruction software user interface. In this illustration, segmentation A delineates thrombus, segmentation B delineates contrast-enhanced bloodflow, segmentation C delineates calcium in the mode.

METHOD FOR DETERMINING THE RISK OF RUPTURE OF A BLOOD VESSEL

REFERENCE TO PENDING PRIOR PATENT APPLICATION

This patent application claims benefit of pending prior U.S. Provisional Patent Application Ser. No. 60/582,128, filed Jun. 23, 2004 by David Chen et al. for METHOD TO CREATE MESH OBJECTS FOR FINITE ELEMENT ANALYSIS OF BLOOD VESSELS AND POST-ANALYSIS STRESS VISUALIZATION, which patent application is hereby incorporated herein by reference.

FIELD OF THE INVENTION

This invention relates to medical apparatus in general, and more particularly to anatomical visualization and measurement systems.

BACKGROUND OF THE INVENTION

Many medical procedures must be carried out at an interior anatomical site which is normally hidden from the view of the physician. In these situations, the physician typically uses some sort of scanning device to examine the patient's anatomy at the interior site prior to, and in preparation for, conducting the actual medical procedure. Such scanning devices typically include CT scanners, MRI devices, X-ray machines, ultrasound devices and the like, and essentially serve to provide the physician with some sort of visualization of the patient's interior anatomical structure prior to commencing the actual medical procedure. The physician can then use this information to plan the medical procedure in advance, taking into account patient-specific anatomical structure.

In addition to the foregoing, the physician can also use the information obtained from such preliminary scanning to more precisely identify the location of selected structures (e.g., tumors and the like) which may themselves be located within the interior of internal organs or other internal body structures. As a result, the physician can then more easily "zero in" on such selected structures during the subsequent medical procedure.

Furthermore, in many cases, the anatomical structures of interest to the physician may be quite small and/or difficult to identify with the naked eye. In these situations, preliminary scanning of the patient's interior anatomical structure using high resolution scanning devices can help the physician locate various structures of interest during the subsequent medical procedure.

In addition to the foregoing, scanning devices of the sort described above are frequently also used in purely diagnostic procedures. For example, scanning devices of the sort described above might be used to look for stenosis in a blood vessel, or the buildup of plaque in a blood vessel, or a thinning of the aorta wall, etc.

In general, scanning devices of the sort described above tend to generate two-dimensional (i.e., "2-D") images of the patient's anatomical structure. In many cases, the scanning devices are adapted to provide a set of 2-D images, with each 2-D image in the set being related to every other 2-D image in the set according to some pre-determined relationship. For example, CT scanners typically generate a series of 2-D images, with each 2-D image corresponding to a specific plane or "slice" taken through the patient's anatomical structure. Furthermore, with many scanning devices, the angle and spacing between adjacent image planes or slices is very well defined, e.g., each image plane or slice may be set parallel to every other image plane or slice, and adjacent image planes or slices may be spaced a pre-determined distance apart. By way of example, the parallel image planes might be set 1 mm apart.

In a system of the sort just described, the physician can view each 2-D image individually and, by viewing a series of 2-D images in proper sequence, can mentally generate a three-dimensional (i.e., "3-D") impression of the patient's interior anatomical structure.

Some scanning devices include, as part of their basic system, associated computer hardware and software for building a 3-D database of the patient's scanned anatomical structure using a plurality of the aforementioned 2-D images. For example, some CT and MRI scanners include such associated computer hardware and software as part of their basic system. Alternatively, such associated computer hardware and software may be provided independently of the scanning devices, as a sort of "add-on" to the system; in this case, the data from the scanned 2-D images is fed from the scanning device to the associated computer hardware and software in a separate step. In either case, a trained operator using such apparatus can create a set of scanned 2-D images, assemble the data from these scanned 2-D images into a 3-D database of the scanned anatomical structure, and then generate various additional images of the scanned anatomical structure using the 3-D database. This feature has been found to be a very powerful tool, since it essentially permits a physician to view the patient's scanned anatomical structure from a wide variety of different viewing positions. As a result, the physician's understanding of the patient's scanned anatomical structure is generally greatly enhanced.

In addition, scanning systems of the sort described above often include hardware and/or software tools to allow measurements to be made of the patient's scanned anatomical structure. By way of example, many of these systems let a physician overlay lines on an image of the patient's anatomical structure, and then calculate the length of these lines so as to indicate the size of the structure being viewed.

While the 2-D slice images generated by the aforementioned scanning devices, and/or the 3-D database images generated by the aforementioned associated computer hardware and software, are generally of great benefit to physicians, certain significant limitations still exist.

For one thing, with current systems, each scanned 2-D slice image is displayed as a separate and distinct image, and each image generated from the 3-D database is displayed as a separate and distinct image. Unfortunately, physicians can sometimes have difficulty correlating what they see on one image with what they see on another image. By way of example but not limitation, physicians can sometimes have difficulty correlating what they see on a particular scanned 2-D slice image with what they see on a particular image generated from the 3-D database.

For another thing, in many situations a physician may be viewing images of a patient's scanned anatomical structure in preparation for conducting a subsequent medical procedure in which a prosthetic device must be fitted in the patient. In these situations it can be relatively difficult and/or time-consuming for the physician to accurately measure and record all of the anatomical dimensions needed for proper sizing of the prosthetic device to the patient. By way of example, in certain situations a patient may develop an abdominal aortic aneurysm ("AAA") in the vicinity of the aorta's iliac branching, and repair or replacement of the affected vascular structure with a prosthetic device may be indicated. In this case it is extremely important for the physician to determine, prior to commencing the procedure, accurate length and cross-sectional dimensions for each affected portion of blood vessel so as to ensure proper sizing of the appropriate prosthetic device to the patient. Unfortunately, it can be difficult and/or impossible to make accurate anatomical measurements with existing visualization systems. This has proven to be particularly true when dealing with anatomical structures which extend along a tortuous path and/or which have a complex and varied branching structure, e.g., blood vessels.

Furthermore, in many cases it may be desirable to provide a physician with a particular oblique view of a specified portion of a patient's anatomical structure. For example, it may be desirable to provide a physician with a view taken perpendicular to the length of a blood vessel, with that view being taken at a very specific location along that blood vessel. Such a view might be desired for comprehensional and/or measurement purposes. Unfortunately, it can be difficult and/or impossible to accurately generate such a view using existing visualization systems.

In addition to the foregoing, in many situations a physician may be interested in accurately calculating a volume associated with a specific part of a patient's anatomy. By way of example but not limitation, a physician might wish to track the volume of a thrombus in an aorta over time, or the size of a tumor during chemotherapy, etc. Unfortunately, it can be difficult and/or impossible to accurately make such a calculation using existing visualization systems.

And in addition to the foregoing, in many situations a physician may be interested in accurately calculating the stress imposed on an anatomical structure and in assessing the risk of rupture of the same.

OBJECTS OF THE INVENTION

Accordingly, one object of the present invention is to provide an improved anatomical visualization and measurement system for visualizing and measuring anatomical structures.

Another object of the present invention is to provide an improved anatomical visualization and measurement system wherein a scanned 2-D slice image can be appropriately combined with an image generated from a 3-D database so as to create a single composite image.

Another object of the present invention is to provide an improved anatomical visualization and measurement system wherein a marker can be placed onto a 2-D slice image displayed on a screen, and this marker will be automatically incorporated, as appropriate, into a 3-D computer model maintained by the system, as well as into any other 2-D slice image data maintained by the system.

Still another object of the present invention is to provide an improved anatomical visualization and measurement system wherein a margin of pre-determined size can be associated with a marker of the sort described above, and further wherein the margin will be automatically incorporated into the 3-D computer model, and into any other 2-D slice image data, in association with that marker.

Yet another object of the present invention is to provide an improved anatomical visualization and measurement system wherein the periphery of objects contained in a 3-D computer model maintained by the system can be automatically identified in any 2-D slice image data maintained by the system, and further wherein the periphery of such objects can be highlighted as appropriate in 2-D slice images displayed by the system.

Another object of the present invention is to provide an improved anatomical visualization and measurement system wherein patient-specific anatomical dimensions such as length and/or cross-sectional dimensions can be quickly, easily and accurately determined.

Still another object of the present invention is to provide an improved anatomical visualization and measurement system which is particularly well adapted to determine patient-specific anatomical dimensions for structures which have a tortuous and/or branching configuration, e.g., blood vessels.

And another object of the present invention is to provide an improved anatomical visualization and measurement system wherein an appropriate set of scanned 2-D images can be assembled into a 3-D database, information regarding patient-specific anatomical structures can be segmented from the information contained in this 3-D database, and this segmented information can then be used to determine anatomical features such as a centerline for the anatomical structure which has been segmented.

Still another object of the present invention is to provide an improved anatomical visualization and measurement system which is able to easily and accurately present a physician with a particular oblique view of a specified portion of a patient's anatomical structure, e.g., a view taken perpendicular to the length of a blood vessel, with that view being taken at a very specific location along that blood vessel.

Another object of the present invention is to provide an improved anatomical visualization and measurement system wherein patient-specific anatomical volumes can be quickly, easily and accurately determined.

And another object of the present invention is to provide an improved anatomical visualization and measurement system wherein an appropriate set of scanned 2-D images can be assembled into a 3-D database, information regarding patient-specific anatomical structures can be segmented from the information contained in this 3-D database, and this segmented information can then be used to calculate desired patient-specific anatomical volumes.

Another object of the present invention is to provide an improved method for visualizing and measuring anatomical structures.

And another object of the present invention is to provide an improved method wherein patient-specific anatomical dimensions such as length and/or cross-sectional dimensions can be quickly, easily and accurately determined.

Still another object of the present invention is to provide an improved method wherein an appropriate set of scanned 2-D images can be assembled into a 3-D database, information regarding patient-specific anatomical structures can be segmented from the information contained in this 3-D database, and this segmented information can then be used to determine anatomical features such as a centerline for the anatomical structure which has been segmented.

And another object of the present invention is to provide a method for easily and accurately presenting a physician with a particular oblique view of a specified portion of a patient's anatomical structure, e.g., a view taken perpendicular to the length of a blood vessel, with that view being taken at a very specific location along that blood vessel.

Yet another object of the present invention is to provide an improved method for quickly, easily and accurately determining patient-specific anatomical volumes.

Yet another object of the present invention is to provide an improved method for calculating the stress on anatomical structures.

SUMMARY OF THE INVENTION

These and other objects are addressed by the present invention, which comprises an anatomical visualization and measurement system comprising a first database which comprises a plurality of 2-D slice images generated by scanning an anatomical structure. These 2-D slice images are stored in a first data format. A second database is also provided which comprises a 3-D computer model of the scanned anatomical structure. This 3-D computer model comprises a first software object which is representative of the scanned anatomical structure and which is defined by a 3-D geometry database.

In one embodiment of the present invention, means are provided for selecting a particular 2-D slice image from the first database. Means are also provided for inserting a second software object into the 3-D computer model so as to augment the 3-D computer model. The second software object is also defined by a 3-D geometry database, and includes a planar surface. In this embodiment of the invention, the second software object is inserted into the 3-D computer model at the position which corresponds to the position of the selected 2-D slice image relative to the scanned anatomical structure. Means for texture mapping the specific 2-D slice image onto the planar surface of the second software object are also provided. Means are also provided for displaying an image of the augmented 3-D computer model so as to simultaneously provide a view of both the first software object and the specific 2-D slice image which has been texture mapped onto the planar surface of the second software object.

In another embodiment of the invention, the system comprises a first database which comprises a plurality of 2-D slice images generated by scanning an anatomical structure. These 2-D slice images are stored in a first data format. A second database is also provided which comprises a 3-D computer model of the scanned anatomical structure. This 3-D computer model comprises a first software object which is representative of the scanned anatomical structure and which is defined by a 3-D geometry database. In this second embodiment of the invention, means are also provided for inserting a second software object into the 3-D computer model so as to augment the 3-D computer model. The second software object is also defined by a 3-D geometry database, and includes a planar surface. Furthermore, means are also provided for determining the specific 2-D slice image which corresponds to the position of the planar surface of the second software object which has been inserted into the augmented 3-D computer model. In this embodiment of the invention, means are also provided for texture mapping the specific 2-D slice image corresponding to the position of that planar surface onto the planar surface of the second software object. In this embodiment of the invention, display means are also provided for displaying an image of the augmented 3-D computer model to a physician so as to simultaneously provide a view of the first software object and the specific 2-D slice image which has been texture mapped onto the planar surface of the second software object.

In each of the foregoing embodiments of the present invention, the 3-D geometry database may comprise a surface model.

Likewise, the system may further comprise means for inserting a marker into the first database, whereby the marker will be automatically incorporated into the second database, and further wherein the marker will be automatically displayed where appropriate in any image displayed by the system.

Also, the system may further comprise a margin of predetermined size associated with the aforementioned marker.

Additionally, the system may further comprise means for automatically identifying the periphery of any objects contained in the second database and for identifying the corresponding data points in the first database, whereby the periphery of such objects can be highlighted as appropriate in any image displayed by the system.

Often, the scanned structure will comprise an interior anatomical structure.

In yet another form of the present invention, the visualization and measurement system may incorporate means for determining patient-specific anatomical dimensions, such as length and/or cross-sectional dimensions, using appropriate scanned 2-D image data. More particularly, the visualization and measurement system may include means for assembling an appropriate set of scanned 2-D images into a 3-D database, means for segmenting information regarding patient-specific anatomical structures from the information contained in the 3-D database, means for determining from this segmented information anatomical features such as a centerline for the anatomical structure which has been segmented, means for specifying a measurement to be made based on the determined anatomical feature, and means for calculating the measurements so specified.

In a more particular form of the present invention, the visualization and measurement system is particularly well adapted to determine patient-specific anatomical dimensions for structures which have a tortuous and/or branching configuration, e.g., blood vessels. In this form of the invention, the visualization and measurement system is adapted to facilitate (1) assembling an appropriate set of scanned 2-D images into a 3-D database; (2) segmenting the volumetric data contained in the 3-D database into a set of 3-D locations corresponding to the specific anatomical structure to be measured; (3) specifying, for each branching structure contained within the specific anatomical structure of interest, a branch line in the volumetric data set that uniquely indicates that branch structure, with the branch line being specified by selecting appropriate start and end locations on two of the set of scanned 2-D images; (4) calculating, for each branching structure contained within the specific anatomical structure of interest, a centroid path in the volumetric data set for that branching structure, with the centroid path being determined by calculating, for each scanned 2-D image corresponding to the branch line, the centroid for the branch structure contained in that particular scanned 2-D image; (5) applying a curve-fitting algorithm to the centroid paths determined above so as to supply data for any portions of the anatomical structure which may lie between the aforementioned branch lines, and for "smoothing out" any noise that may occur in the system; and (6) applying known techniques to the resulting space curves so as to determine the desired anatomical dimensions.

In still another form of the present invention, the visualization and measurement system may incorporate means for easily and accurately presenting a physician with a particular oblique view of a specified portion of a patient's anatomical structure, e.g., a view taken perpendicular to a blood vessel, at a very specific location along that blood vessel.

In another form of the present invention, the visualization and measurement system may incorporate means for more accurately measuring the dimensions of an anatomical structure by utilizing one or more oblique views taken along the length of that anatomical structure.

In yet another form of the present invention, the visualization and measurement system may incorporate means for determining patient-specific anatomical volumes using appropriate scanned 2-D image data. More particularly, the visualization and measurement system may include means for assembling an appropriate set of scanned 2-D images into a 3-D database, means for segmenting information regarding patient-specific anatomical structures from the information contained in the 3-D database, means for determining from this segmented information anatomical volumes from the anatomical structure which has been segmented, means for specifying a structure of interest, and means for calculating the volume of the specified structure.

The present invention also comprises an improved method for visualizing and measuring anatomical structures.

The present invention also comprises a method for calculating patient-specific anatomical dimensions using appropriate scanned 2-D image data. In one form of the present invention, the method comprises the steps of (1) assembling an appropriate set of scanned 2-D images into a 3-D database; (2) segmenting information regarding patient-specific anatomical structures from the information contained in the 3-D database, (3) determining for this segmented information anatomical features such as a centerline for the anatomical structure which has been segmented; (4) specifying a measurement to be made based on the determined anatomical feature; and (5) calculating the measurement so specified.

The present invention also comprises a method for easily and accurately presenting a physician with a particular oblique view of a specified portion of a patient's anatomical structure, e.g., a view taken perpendicular to a blood vessel, at a very specific location along that blood vessel.

The present invention also comprises a method for calculating patient-specific anatomical volumes using appropriate scanned 2-D image data. In one form of the present invention, the method comprises the steps of (1) assembling an appropriate set of scanned 2-D images into a 3-D database; (2) segmenting information regarding patient-specific anatomical structures from the information contained in the 3-D database, (3) determining from this segmented information volumes for the anatomical structure which has been segmented, (4) specifying a structure of interest, and (5) calculating the volume of the specified structure.

In another preferred form of the present invention, there is provided a method for determining the risk of rupture of a blood vessel using an appropriate set of 2-D slice images obtained by scanning the blood vessel, the method comprising:

generating a mesh model of the blood vessel using the set of 2-D slice images;

conducting finite element stress analysis on the mesh model to calculate the level of stress on different locations on the mesh model; and determining the risk of rupture of the blood vessel based on the calculated levels of stress on different locations on the mesh model.

In another preferred form of the present invention, there is provided an apparatus for determining the risk of rupture of a blood vessel using an appropriate set of 2-D slice images obtained by scanning the blood vessel, the apparatus comprising:

apparatus for generating a mesh model of the blood vessel using the set of 2-D slice images;

apparatus for conducting finite element stress analysis on the mesh model to calculate the level of stress on different locations on the mesh model; and apparatus for determining the risk of rupture of the blood vessel based on the calculated levels of stress on different locations on the mesh model.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENT

Basic System

Figure 1:
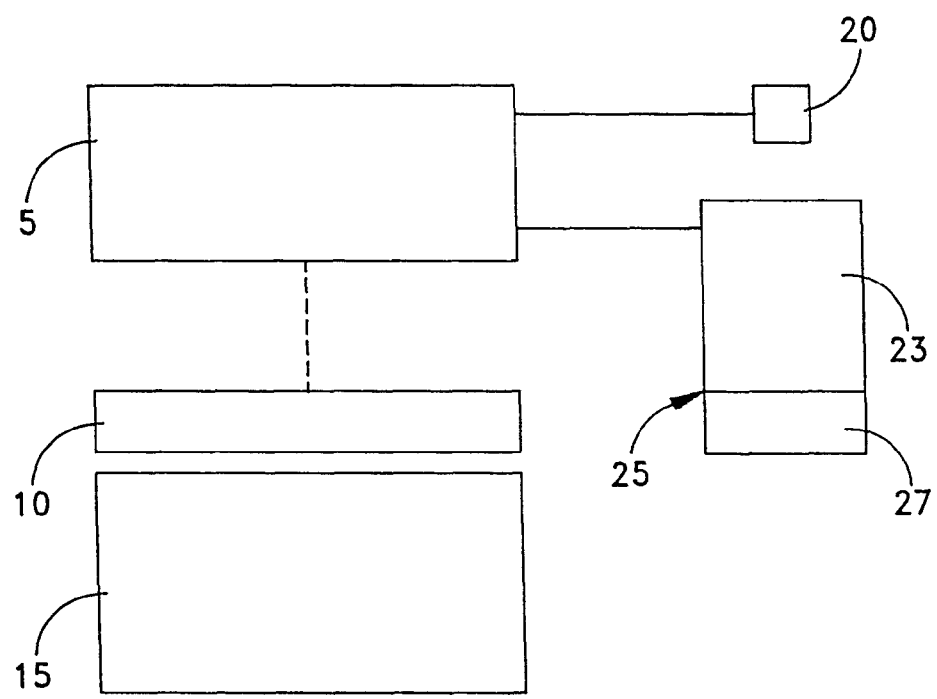
FIG. 1 is a schematic view showing a scanning device for generating a set of 2-D images of the anatomy of a patient.

Looking first at FIG. 1, a scanning device 5 is shown as it scans the interior anatomical structure of a patient 10, as that patient 10 lies on a scanning platform 15.

Scanning device 5 is of the sort adapted to generate scanning data corresponding to a series of 2-D images, where each 2-D image corresponds to a specific viewing plane or "slice" taken through the patient's body. Furthermore, scanning device 5 is adapted so that the angle and spacing between adjacent image planes or slices can be very well defined, e.g., each image plane or slice may be set parallel to every other image plane or slice, and adjacent image planes or slices may be spaced a pre-determined distance apart. By way of example, the parallel image planes might be set 1 mm apart.

The scanning data obtained by scanning device 5 can be displayed as a 2-D slice image on a display 20, and/or it can be stored in its 2-D slice image data form in a first section 23 of a data storage device or medium 25. Furthermore, additional information associated with the scanning data (e.g., patient name, age, etc.) can be stored in a second section 27 of data storage device or medium 25.

By way of example, scanning device 5 might comprise a CT scanner of the sort manufactured by GE Medical Systems of Milwaukee, Wis.

Figure 2:
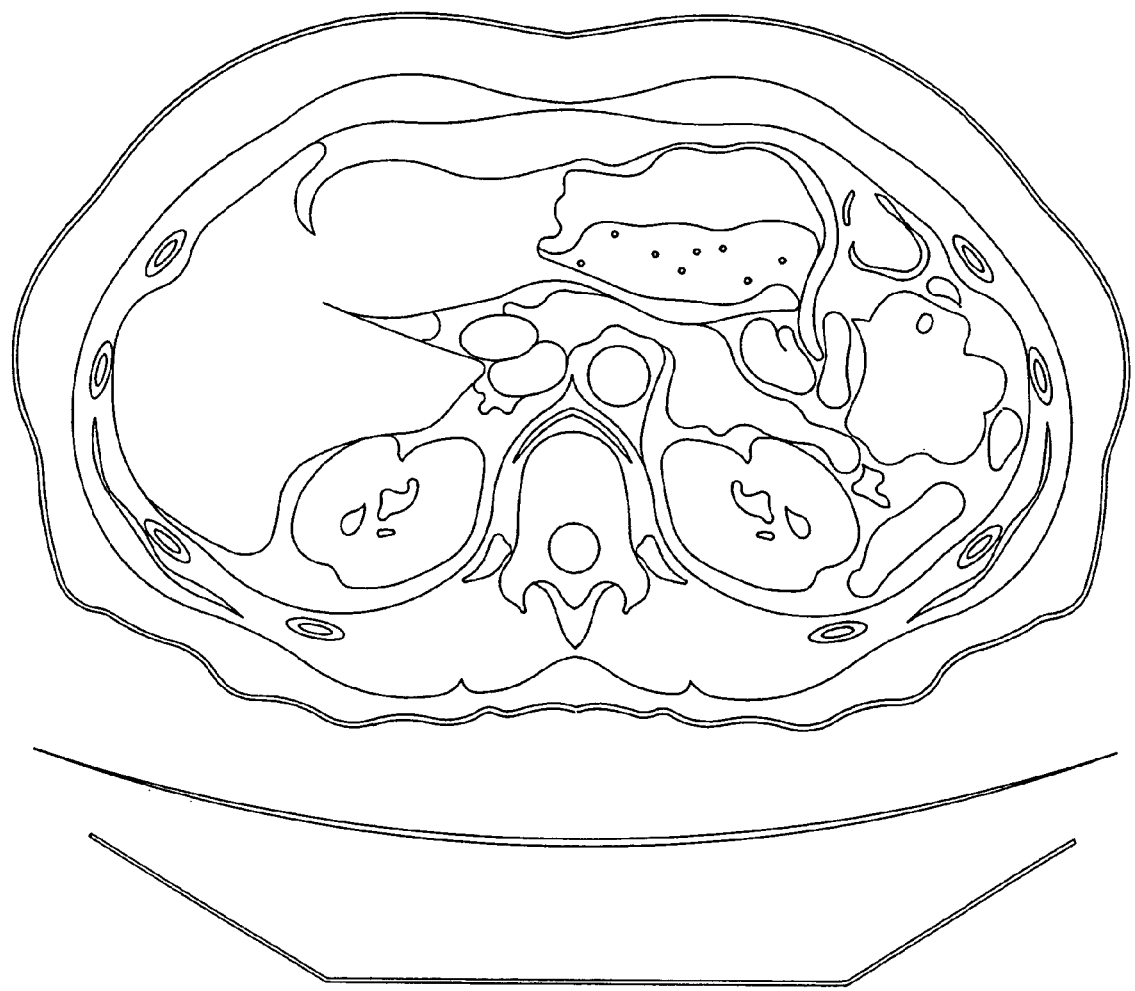
FIG. 2 is a 2-D slice image corresponding to an axial slice taken through the abdomen of an individual.

By way of further example, a 2-D slice image of the sort generated by scanning device 5 and displayed on display 20 might comprise the 2-D slice image shown in FIG. 2. In the particular example shown in FIG. 2, the 2-D slice image shown corresponds to an axial slice taken through an individual's abdomen and showing, among other things, that individual's liver.

Scanning device 5 may format its scanning data in any one of a number of different data structures. By way of example, scanning device 5 might format its scanning data in the particular data format used by a CT scanner of the sort manufactured by GE Medical Systems of Milwaukee, Wis. More specifically, with such a scanning device, the scanning data is generally held as a series of data "frames", where each data frame corresponds to a particular 2-D slice image taken through the patient's body. Furthermore, within each data frame, the scanning data is generally organized so as to represent the scanned anatomical structure at a particular location within that 2-D slice image. Such a data structure is fairly common for scanning devices of the sort associated with the present invention. However, it should be appreciated that the present invention is not dependent on the particular data format utilized by scanning device 5. For the purposes of the present invention, the scanning data provided by scanning device 5 can be formatted in almost any desired data structure, so long as that data structure is well defined, whereby the scanning data can be retrieved and utilized as will hereinafter be disclosed in further detail.

Figure 3:
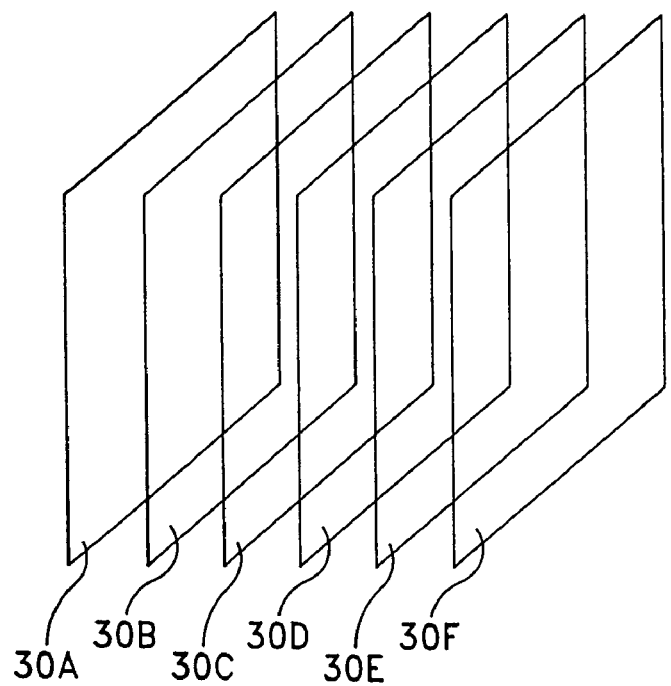
FIG. 3 shows a series of data frames corresponding to 2-D slice images arranged in a parallel array.
Figure 4:
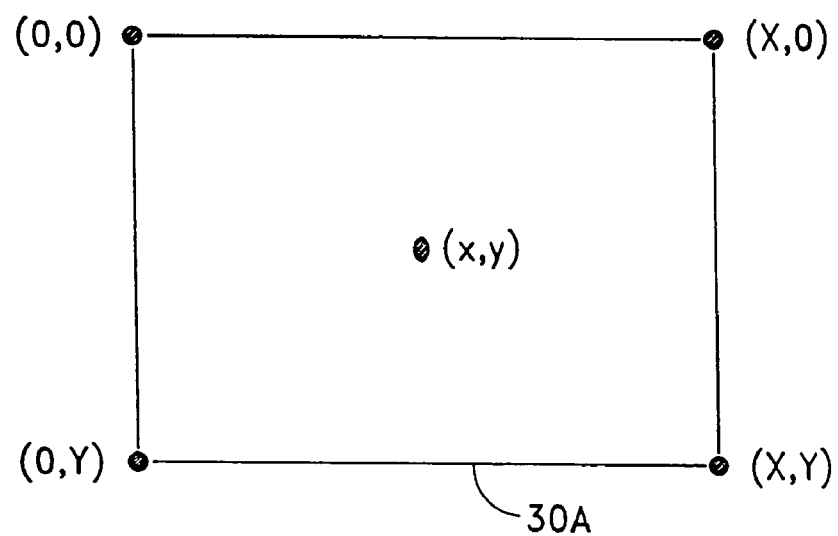
FIG. 4 is a schematic view showing the scanning data contained within an exemplary data frame.

For purposes of illustrating the present invention, it can be convenient to think of the scanning data generated by scanning device 5 as being organized in the data structures schematically illustrated in FIGS. 3 and 4.

More particularly, in FIG. 3, a series of data frames 30A, 30B, 30C, etc. are shown arranged in a parallel array. Each of these data frames 30A, 30B, 30C, etc. corresponds to a particular 2-D slice image taken through the patient's body by scanning device 5, where the 2-D slice images are taken parallel to one another. In addition, adjacent image planes or slices are spaced apart by a constant, pre-determined distance, e.g., 1 mm. It will be appreciated that data frames 30A, 30B, 30C, etc. collectively form a volumetric data set which is representative of the patient's scanned anatomical structure.

Furthermore, in FIG. 4, the scanning data contained within an exemplary data frame 30A is shown represented in an X-Y coordinate scheme so as to quickly and easily identify the scanned anatomical structure disposed at a particular location within that 2-D slice image. Typically, the scanning data relating to a particular X-Y coordinate represents an image intensity value. This image intensity value generally reflects some attribute of the specific anatomical structure being scanned, e.g., the tissue density.

As noted above, the scanning data generated by scanning device 5 is stored in its 2-D slice image data form in first section 23 of data storage device or medium 25, with the scanning data being stored in a particular data format as determined by the manufacturer of scanning device 5.

Figure 5:
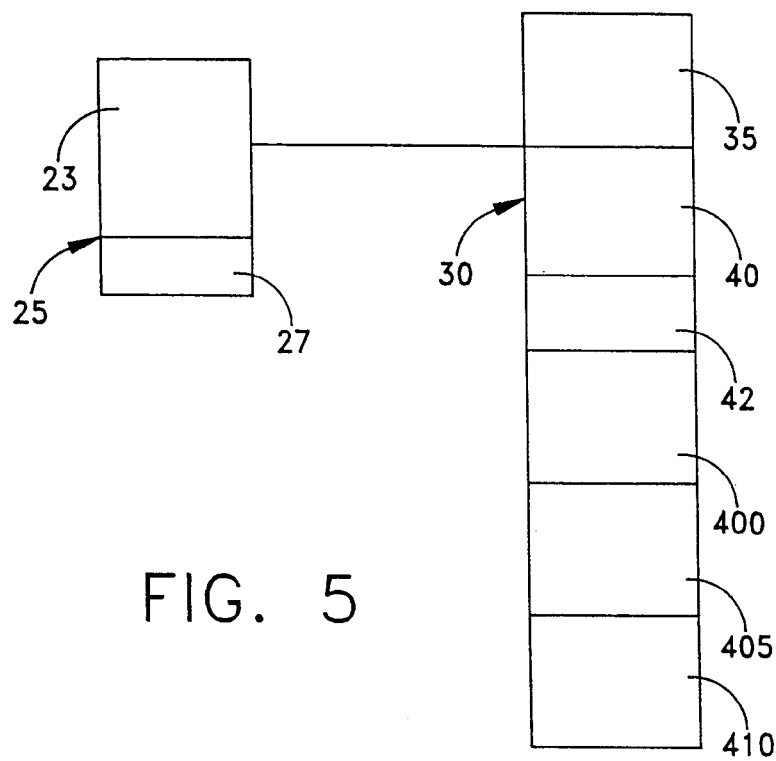
FIG. 5 shows scanning data stored in a first storage device or medium being retrieved, processed and then stored again in a second data storage device or medium.

In accordance with the present invention, and looking now at FIG. 5, the scanning data stored in first section 23 of data storage device or medium 25 is retrieved, processed and then stored again in a data storage device or medium 30.

More particularly, the scanning data stored in first section 23 of data storage device or medium 25 is retrieved and processed so as to convert the scanning data generated by scanning device 5 from its 2-D slice image data form into a 3-D computer model of the patient's anatomical structure. This 3-D computer model is then stored in a first section 35 of data storage device or medium 30.

In addition, the scanning data stored in first section 23 of data storage device or medium 25 is retrieved and processed as necessary so as to convert the scanning data into a preferred data format for the 2-D slice image data. The 2-D slice image data is then stored in this preferred data format in second section 40 of data storage device or medium 30.

Furthermore, the additional information associated with the scanning data (e.g., patient name, age, etc.) which was previously stored in second section 27 of data storage device or medium 25 can be stored in a third section 42 of data storage device or medium 30.

In accordance with the present invention, once the 3-D computer model has been stored in first section 35 of data storage device or medium 30, and the 2-D slice image data has been stored in a preferred data format in second section 40 of data storage device or medium 30, a physician can then use an appropriately programmed computer to access the 3-D computer model stored in first section 35 of data storage device or medium 30, and/or the 2-D slice image data stored in second section 40 of data storage device or medium 30, to generate desired patient-specific images.

Figure 6:
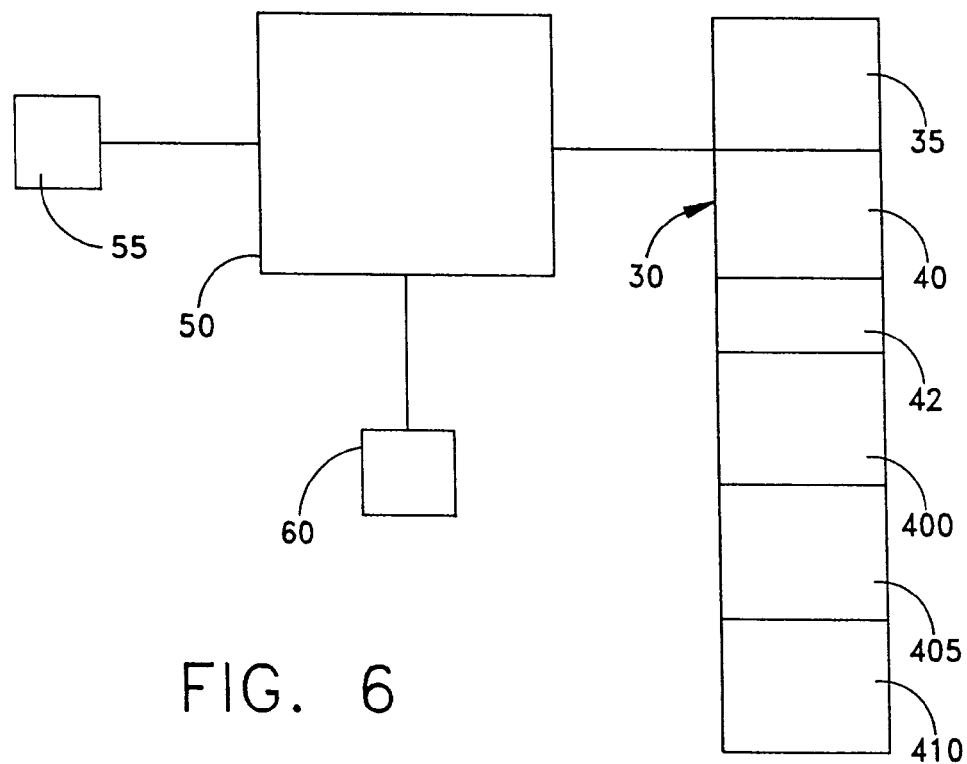
FIG. 6 is a schematic view of a system for retrieving and viewing scanning data.

More particularly, and looking now at FIG. 6, once the 3-D computer model has been stored in first section 35 of data storage device or medium 30, and the 2-D slice image data has been stored in a preferred data format in second section 40 of data storage device or medium 30, a physician can use an appropriately programmed computer 50, operated by input devices 55, to access the 3-D computer model stored in first section 35 of data storage device or medium 30, and/or the 2-D slice image data stored in second section 40 of data storage device or medium 30, so as to generate the desired patient-specific images and display those images on a display 60.

To this end, it will be appreciated that the specific data structure used to store the 3-D computer model in first section 35 of data storage device or medium 30, and the specific data structure used to store the 2-D slice image data in second section 40 of data storage device or medium 30, will depend on the specific nature of computer 50 and on the particular operating system and application software being run on computer 50.

Figure 7:
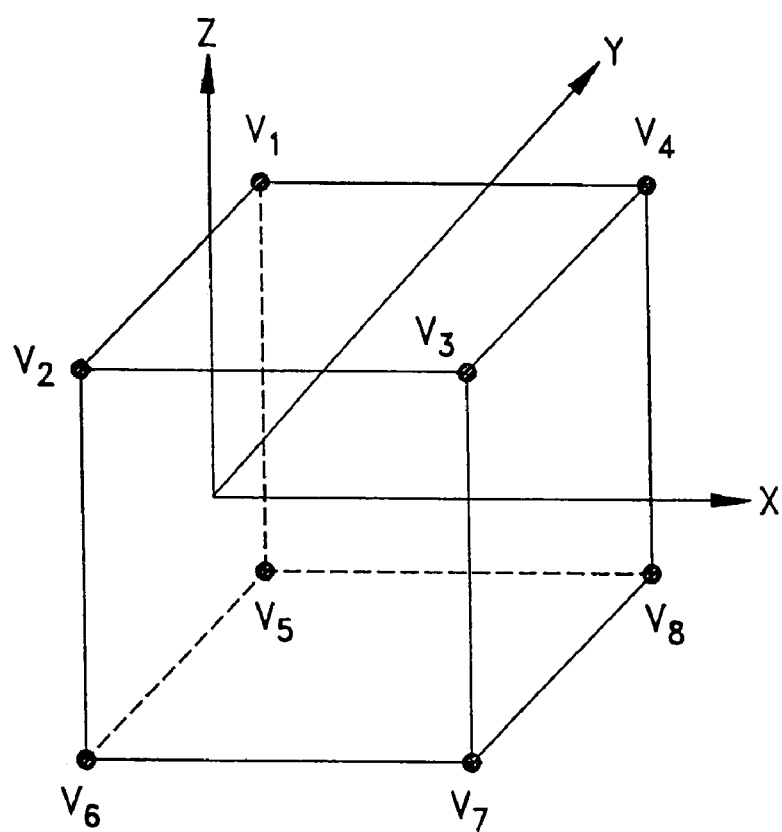
FIG. 7 is a schematic view of a unit cube for use in defining polygonal surface models.
Figure 8:
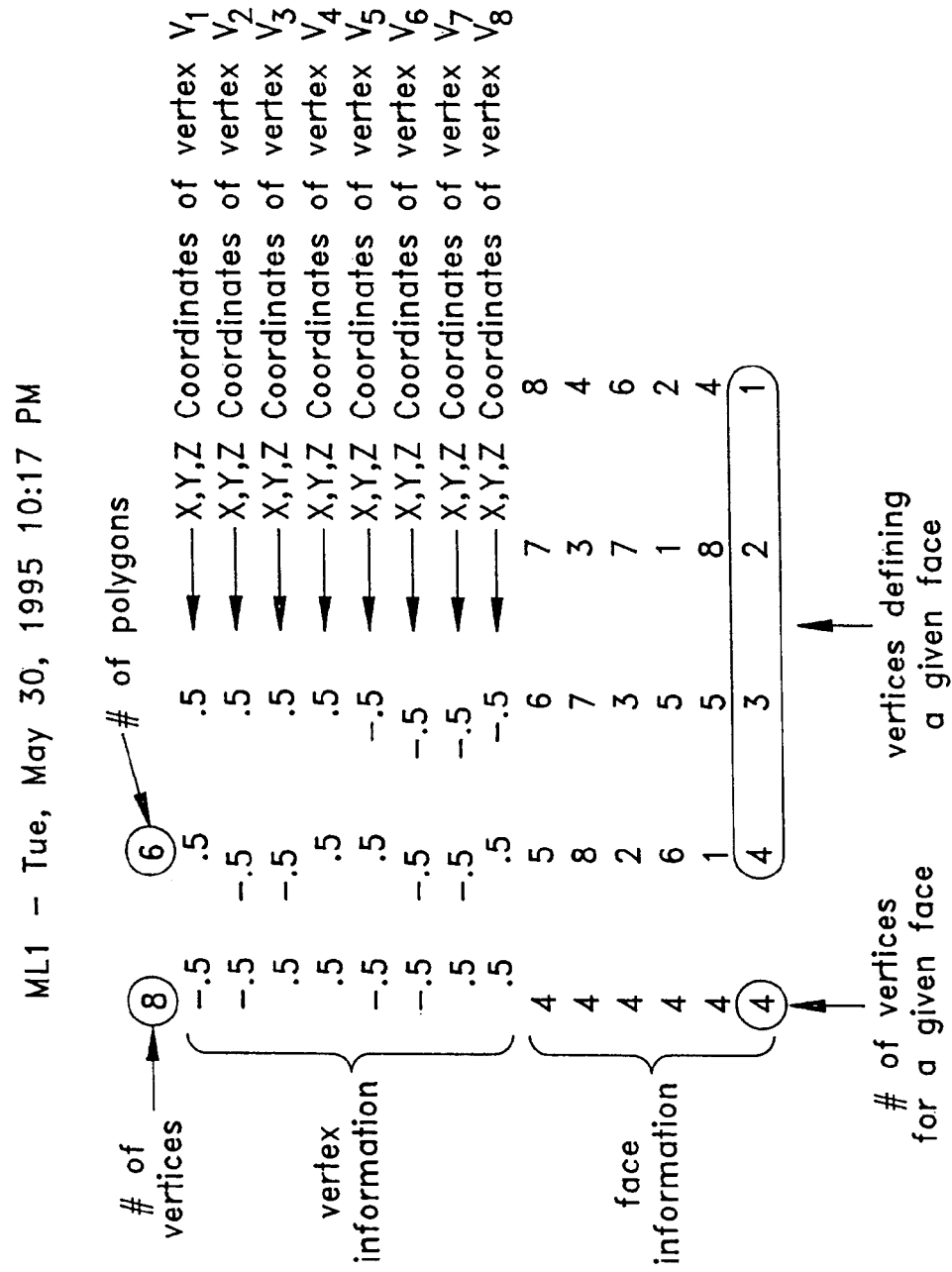
FIG. 8 illustrates the data file format of the polygonal surface model for the simple unit cube shown in FIG. 7.
Figure 9A:
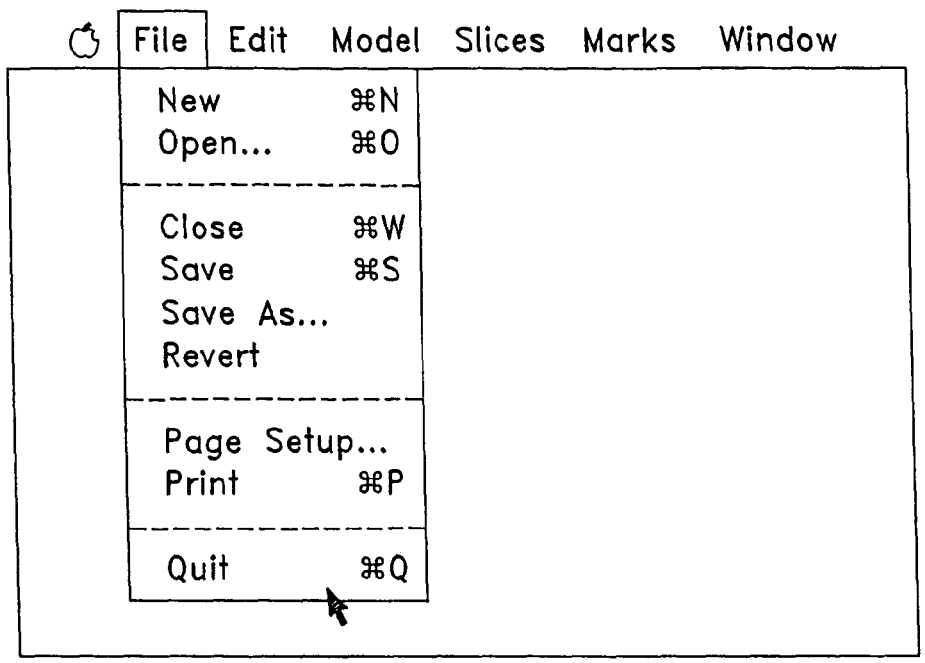
FIGS. 9A-9F illustrate a variety of menu choices which may be utilized in connection with the present invention.
Figure 9B:
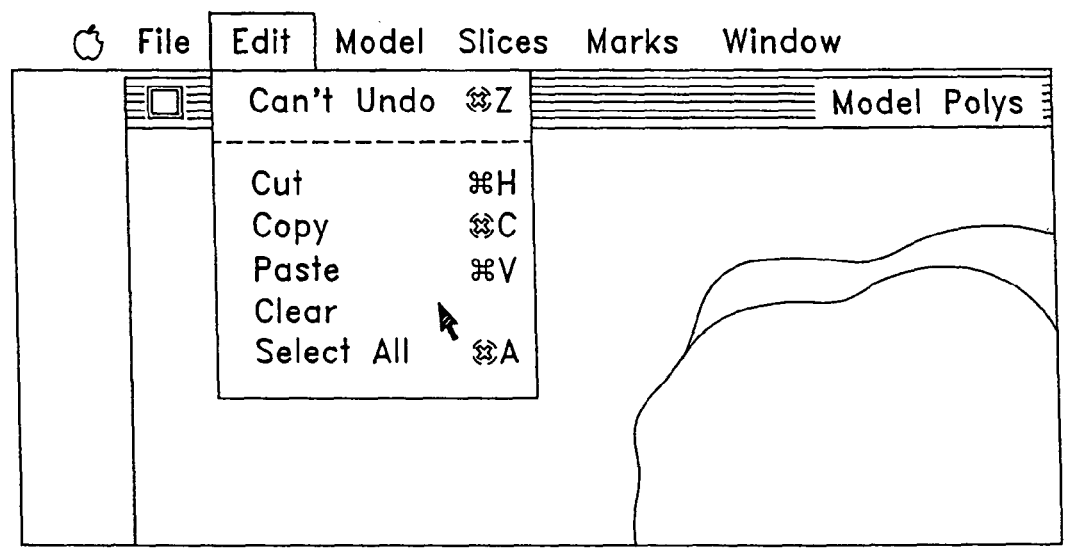
Figure 9C:
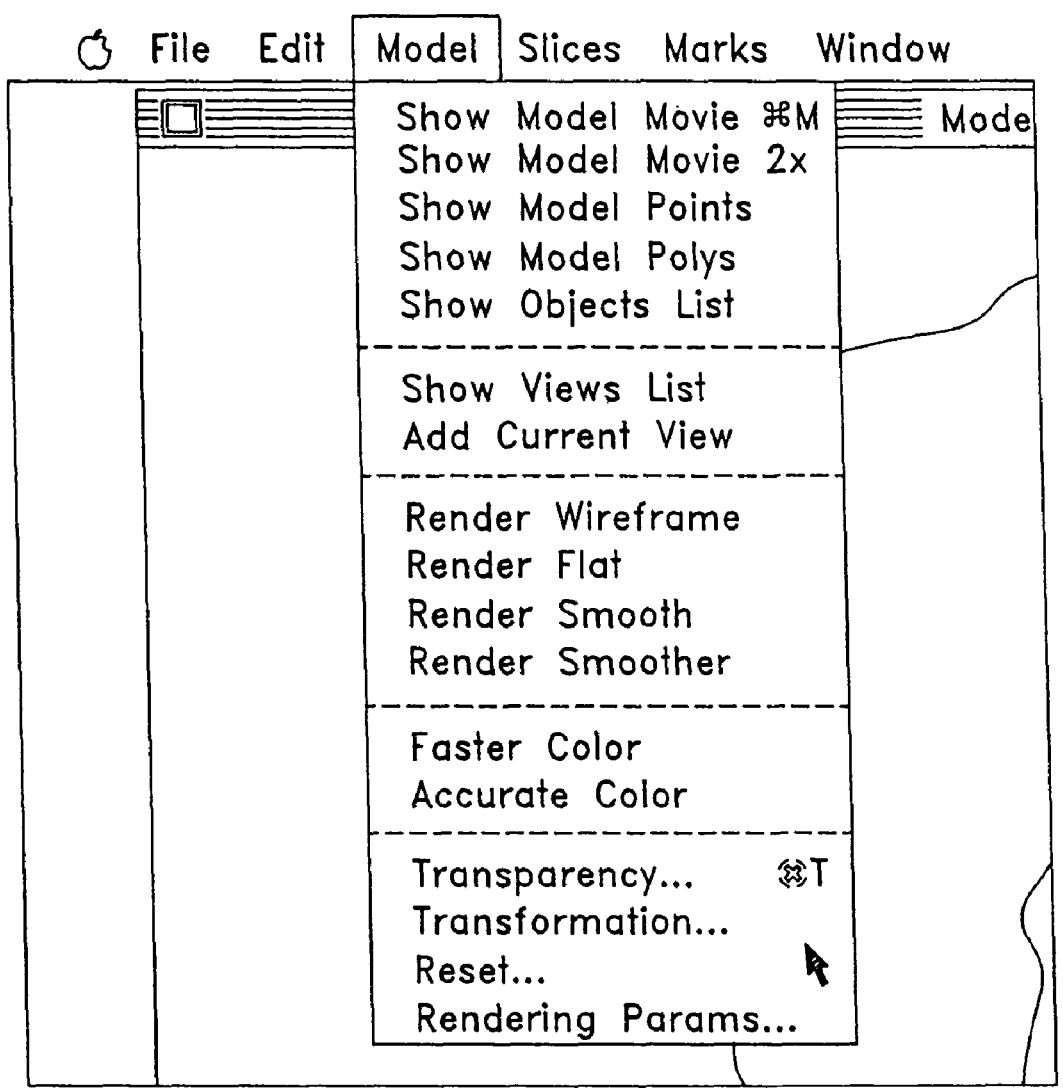
Figure 9D:
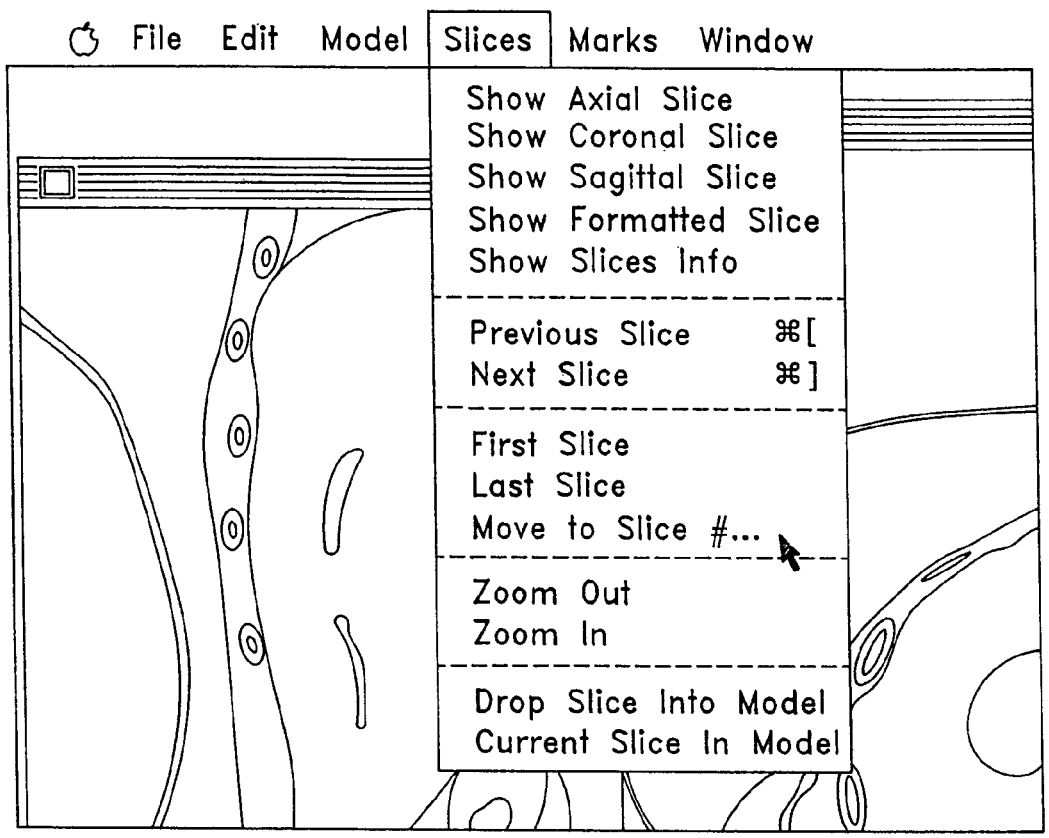
Figure 9E:
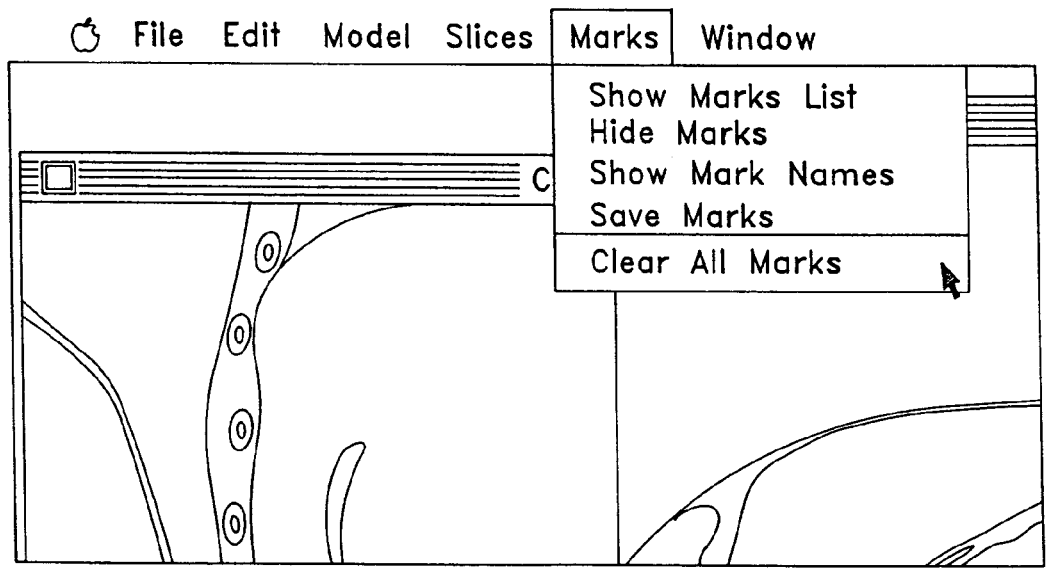
Figure 9F:
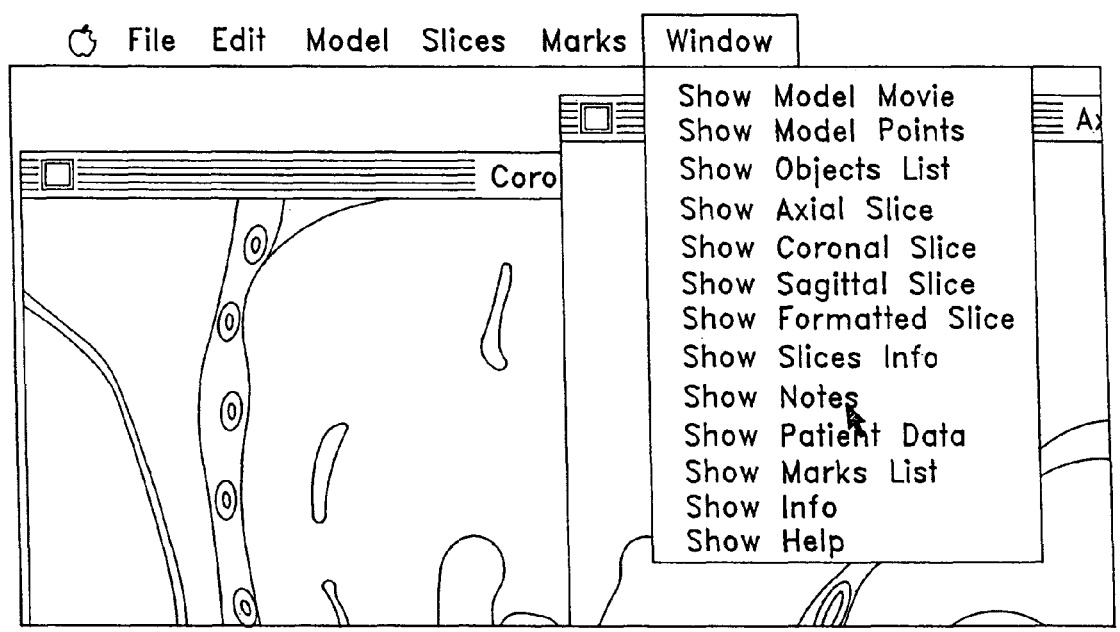

In general, however, the 3-D computer model contained in first section 35 of data storage device or medium 30 is preferably structured as a collection of software objects, with each software object being defined by a polygonal surface model of the sort well known in the art. By way of example, a scanned anatomical structure such as a human liver might be modeled as three distinct software objects, with the outer surface of the general mass of the liver being one software object, the outer surface of the vascular structure of the liver being a second software object, and the outer surface of a tumor located in the liver being a third software object. By way of further example, FIGS. 7 and 8 illustrate a typical manner of defining a software object by a polygonal surface model. In particular, FIG. 7 illustrates the vertices of a unit cube set in an X-Y-Z coordinate system, and FIG. 8 illustrates the data file format of the polygonal surface model for this simple unit cube. As is well known in the art, more complex shapes such as human anatomical structure can be expressed in corresponding terms.

Furthermore, the 3-D computer model contained in first section 35 of data storage device or medium 30 is created by analyzing the 2-D slice image data stored in first section 23 of data storage device or medium 25 using techniques well known in the art. For example, the 2-D slice image data stored in first section 23 of data storage device or medium 25 might be processed using the well known "Marching Cubes" algorithm, which is a so-called "brute force" surface construction algorithm that extracts isodensity surfaces from a volumetric data set, producing from one to five triangles within voxels that contain the surface. Alternatively, the 2-D slice image data stored in first section 23 of data storage device or medium 25 might be processed into the 3-D computer model stored in first section 35 of data storage device or medium 30 by some other appropriate modeling algorithm so as to yield the desired 3-D computer model which is stored in first section 35 of data storage device or medium 30.

As noted above, the specific data structure used to store the 2-D slice image data in second section 40 of data storage device or medium 30 will also depend on the specific nature of computer 50 and on the particular operating system and application software being run on computer 50.

In general, however, the 2-D slice image data contained in second section 40 of data storage device or medium 30 is preferably structured as a series of data "frames", where each data frame corresponds to a particular 2-D slice image taken through the patient's body, and where the scanning data within each data frame is organized so as to represent the scanned anatomical structure at a particular location within that 2-D slice image.

In the present invention, it is preferred that computer 50 comprise a Power PC-based, Macintosh operating system ("Mac OS") type of computer, e.g. a Power PC Macintosh 8100/80 of the sort manufactured by Apple Computer, Inc. of Cupertino, Calif. In addition, it is preferred that computer 50 be running Macintosh operating system software, e.g. Mac OS Ver. 7.5.1, such that computer 50 can readily access a 3-D computer model formatted in Apple's well-known QuickDraw 3D data format and display images generated from that 3D computer model, and such that computer 50 can readily access and display 2-D images formatted in Apple's well-known QuickTime image data format. Input devices 55 preferably comprise the usual computer input devices associated with a Power PC-based, Macintosh operating system computer, e.g., input devices 55 preferably comprise a keyboard, a mouse, etc.

In view of the foregoing, in the present invention it is also preferred that the 3-D computer model contained in first section 35 of data storage device or medium 30 be formatted in Apple's QuickDraw 3D data format, whereby the Mac OS computer 50 can quickly and easily access the 3-D computer model contained in first section 35 of data storage device or medium 30 and display images generated from that 3-D computer model on display 60.

In view of the foregoing, in the present invention it is also preferred that the 2-D slice image data contained in second section 40 of data storage device or medium 30 be formatted in Apple's QuickTime image data format. In this way computer 50 can quickly and easily display the scanned 2-D slice images obtained by scanning device 5. It will be appreciated that, to the extent that scanning device 5 happens to format its scanning data in the preferred QuickTime image data format, no reformatting of the 2-D slice image data will be necessary prior to storing the 2-D slice image data in second section 40 of data storage device or medium 30. However, to the extent that scanning device 5 happens to format its scanning data in a different data structure, reformatting of the 2-D slice image data will be necessary so as to put it into the preferred Quick-Time image data format. Such image data reformatting is of the sort well known in the art.

As a result of the foregoing, it will be seen that a physician operating computer 50 through input devices 55 can generate a desired image from the 3-D computer model contained within first section 35 of data storage device or medium 30. In particular, the physician can use input devices 55 to (1) open a window on display 60, (2) instruct the computer as to the desired angle of view, (3) generate the corresponding image of the scanned anatomical structure from the desired angle of view, using the 3-D computer model contained within first section 35 of data storage device or medium 30, and (4) display that image in the open window on display 60.

In addition, a physician operating computer 50 through input devices 55 can display a desired 2-D slice image from the 2-D slice image data contained within second section 40 of data storage device or medium 30. In particular, the physician can use input devices 55 to (1) open a window on display 60, (2) select a particular 2-D slice image contained within second section 40 of data storage device or medium 30, and (3) display that slice image in the open window on display 60.

More particularly, and looking now at FIGS. 9A-9F, computer 50 is preferably programmed so as to provide a variety of pre-determined menu choices which may be selected by the physician operating computer 50 via input devices 55.

Figure 10:
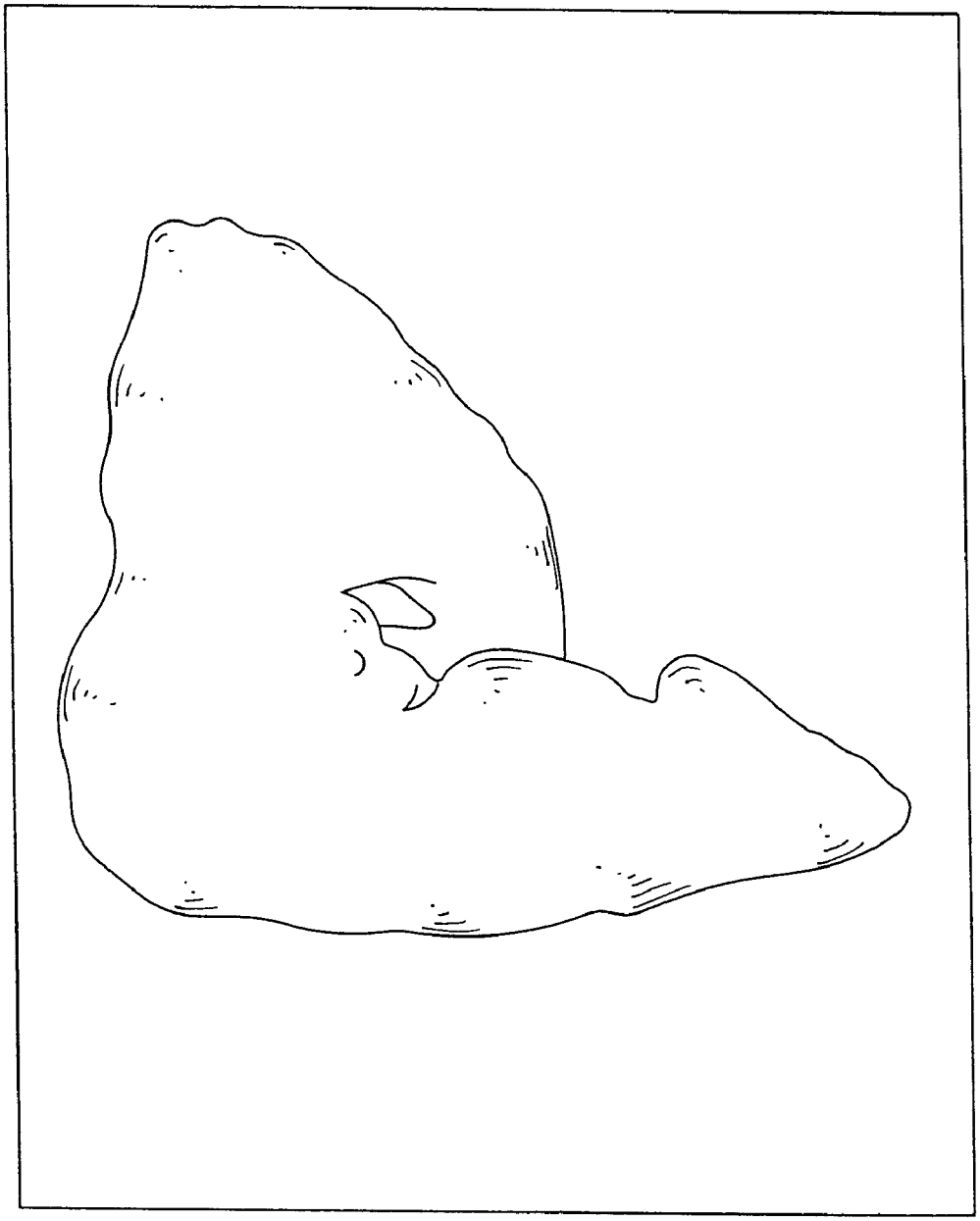
FIG. 10 illustrates an image drawn to a window using the data contained in the 3-D computer model associated with the present invention.

Thus, for example, if the physician wishes to produce a desired image from the 3-D computer model contained within first section 35 of data storage device or medium 30, the physician uses input devices 55 to invoke the command to display the 3-D computer model; the software then creates a window to display the image, it renders an image from the 3-D computer model contained within first section 35 of data storage device or medium 30, and then displays that image in the open window on display 60. By way of example, FIG. 10 illustrates an image drawn to a window using the data contained in the 3-D computer model stored in first section 35 of data storage device or medium 30. The physician can use input devices 55 to instruct the image rendering software as to the specific angle of view desired. In particular, computer 50 is preferably programmed so that the physician can depress a mouse key and then drag on the object so as to rotate the object into the desired angle of view. Additionally, computer 50 is preferably programmed so that the physician can also use the keyboard and mouse to move the view closer in or further out, or to translate the object side to side or up and down relative to the image plane. Programming to effect such computer operation is of the sort well known in the art.

Figure 11:
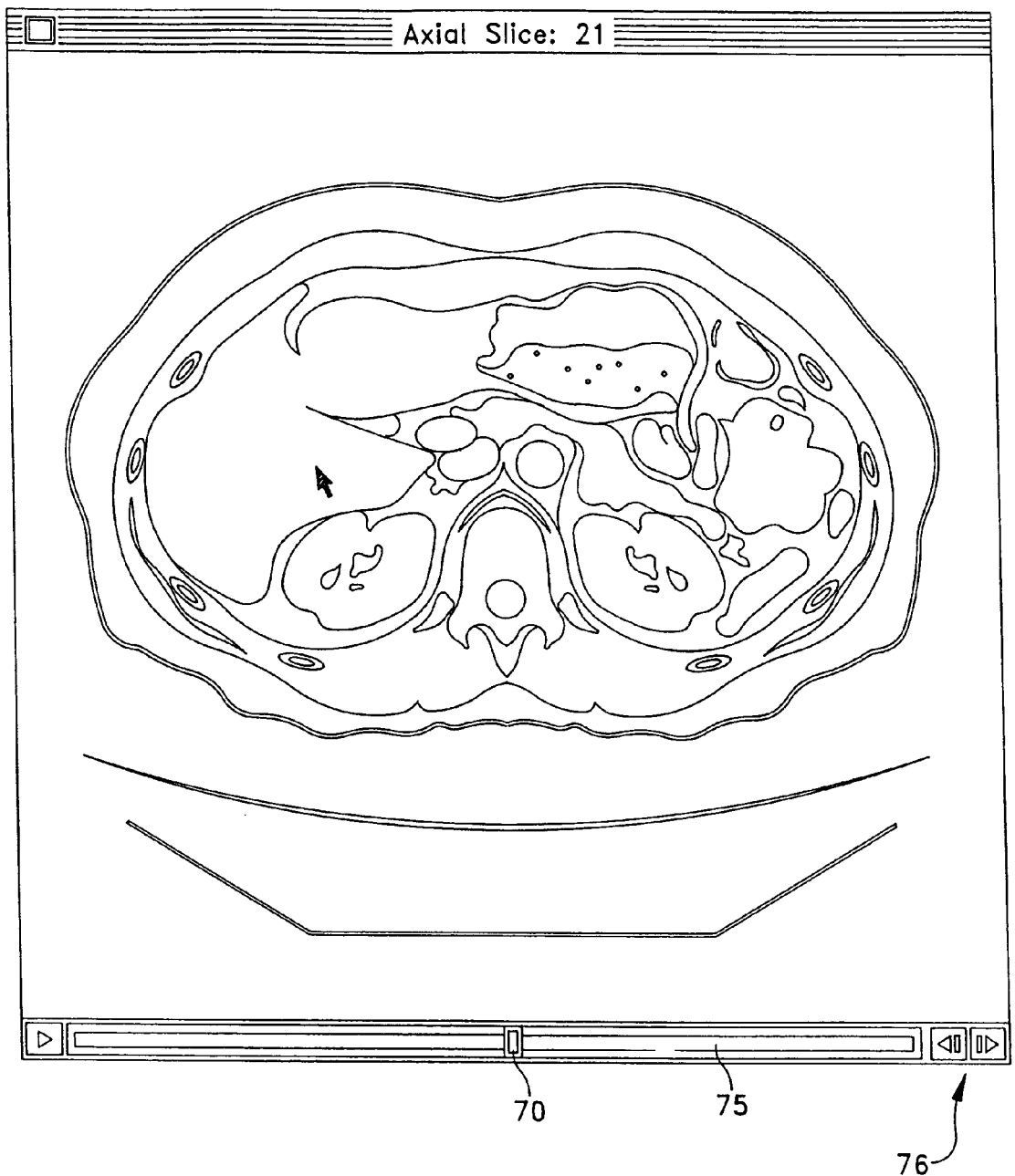
FIG. 11 illustrates a 2-D slice image drawn to a window in accordance with the present invention.

In a similar manner, the physician can use menu choices such as those shown in FIGS. 9A-9F to open a window on the display 60 and then to display in that window a desired 2-D slice image from second section 40 of data storage device or medium 30. Computer 50 is programmed so that the physician can select between different slice images by means of input devices 55. By way of example, FIG. 11 illustrates a 2-D slice image drawn to a window by the operating system using the data contained in second section 40 of data storage device or medium 30. In this case, computer 50 is programmed so that, by dragging icon 70 back and forth along slider 75, the physician can "leaf" back and forth through the collection of axial slices, i.e., in the example of FIG. 11, in which axial slice #21 is displayed, dragging icon 70 to the left might cause axial slice #20 to be displayed, and dragging icon 70 to the right might cause axial slice #22 to be displayed. Additionally, computer 50 is preferably programmed so that the physician can also step the image from the current slice number to a previous or following slice number by using menu commands or by clicking the mouse cursor on the single step icons 76 set at the right side of slider 75. Computer 50 is preferably also programmed so that menu commands are provided to change the slice window display directly to the first or last slice image in the 2-D slice image set, or to change the slice window display to a user-specified slice number. Programming to effect such computer operation is of the sort well known in the art.

Figure 12:
FIG. 12 illustrates a composite image formed from information contained in both the 3-D computer model and the 2-D slice image data structure.

As a consequence of using the aforementioned hardware and software architecture (i.e., the Macintosh computer, the Mac OS, the Apple QuickDraw 3D data format and software, and the Apple QuickTime image data format and software, or some equivalent hardware and software), it is possible to insert an additional software object into the 3-D computer model contained within first section 35 of data storage device or medium 30. In particular, it is possible to insert an additional software object having a "blank" planar surface into the 3-D computer model. Furthermore, using the computer's image rendering software, it is possible to texture map a 2-D slice image from second section 40 of data storage device or medium 30 onto the blank planar surface of the inserted software object. Most significantly, since the 3-D computer model is created out of the same scanning data as the 2-D slice images, it is possible to determine the specific 2-D slice image which corresponds to a given position of the blank planar surface within the 3-D computer model. Accordingly, with the present invention, when an image is generated from the 3-D computer model, both 3-D model structure and 2-D slice image structure can be simultaneously displayed in proper registration with one another, thereby providing a single composite image of the two separate images. See, for example, FIG. 12, which shows such a composite image. Again, computer 50 is programmed so that the physician can use input devices 55 to instruct the operating system's image rendering software as to where the aforementioned "additional" software object is to be inserted into the model and as to the particular angle of view desired. Programming to effect such computer operation is of the sort well known in the art.

Additionally, computer 50 is also programmed so that (1) the physician can use input devices 55 to select a particular 2-D slice image from the second section 40 of data storage device or medium 30, and (2) the computer will then automatically insert the aforementioned additional software object into the 3-D computer model so that the object's "blank" planar surface is located at the position which corresponds to the position of the selected 2-D slice image relative to the scanned anatomical structure. Again, programming to effect such computer operation is of the sort well known in the art.

In the foregoing description of the present invention, the 2-D slice image data generated by scanning device 5 has generally been discussed in the context of the standard "axial" slice images normally generated by scanning devices of the type associated with this invention. However, it is to be appreciated that the present invention is also adapted to utilize sagittal and/or coronal 2-D slice images. Furthermore, it is also to be appreciated that the present invention is adapted to utilize oblique slice images of the type hereinafter described.

Figure 13:
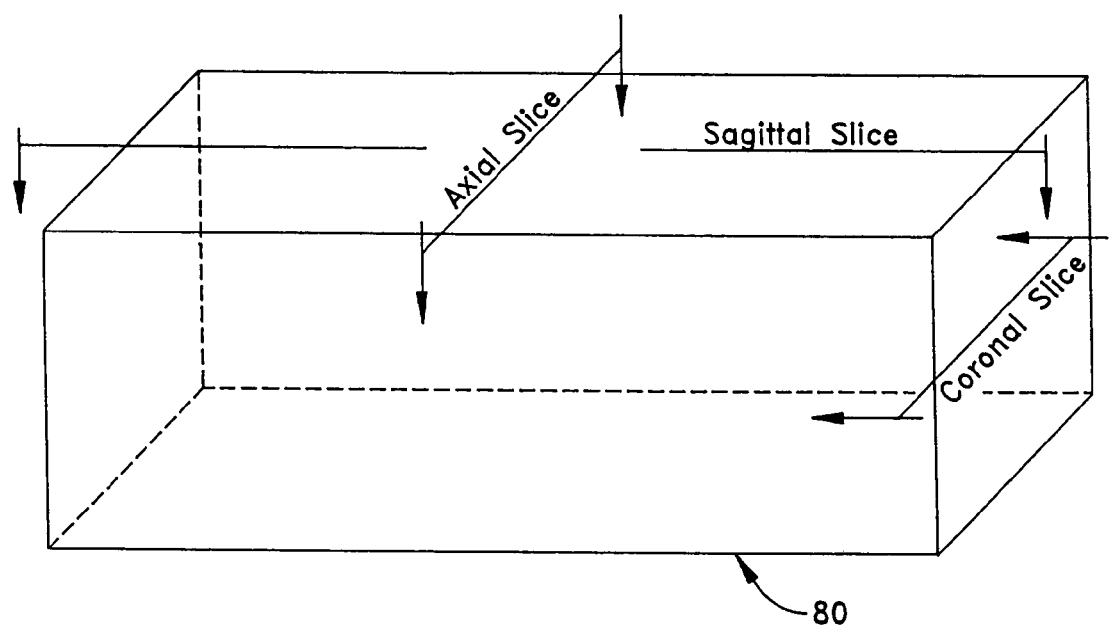
FIG. 13 is a schematic illustration showing the relationship between axial slices, sagittal slices and coronal slices.

More particularly, and looking next at FIG. 13, the relative orientation of axial, sagittal and coronal slice images are shown in the context of a schematic view of a human body 80. Scanning device 5 will normally generate axial slice image data when scanning a patent. In addition, in many cases scanning device 5 will also assemble the axial slice data into a 3-D database (i.e., a volumetric data set) of the scanned anatomical structure, and then use this 3-D database to generate a corresponding set of sagittal and/or coronal 2-D slice images. In the event that scanning device 5 does not have the capability of generating the aforementioned sagittal and/or coronal 2-D slice images, such sagittal and/or coronal 2-D slice images may be generated from a set of the axial 2-D images in a subsequent operation, using computer hardware and software of the sort well known in the art. Alternatively, if desired, computer 50 may be programmed to render such sagittal and/or coronal 2-D slices "on the fly" from the 2-D slice image data contained in second section 40 of data storage device or medium 30.

Figure 14:
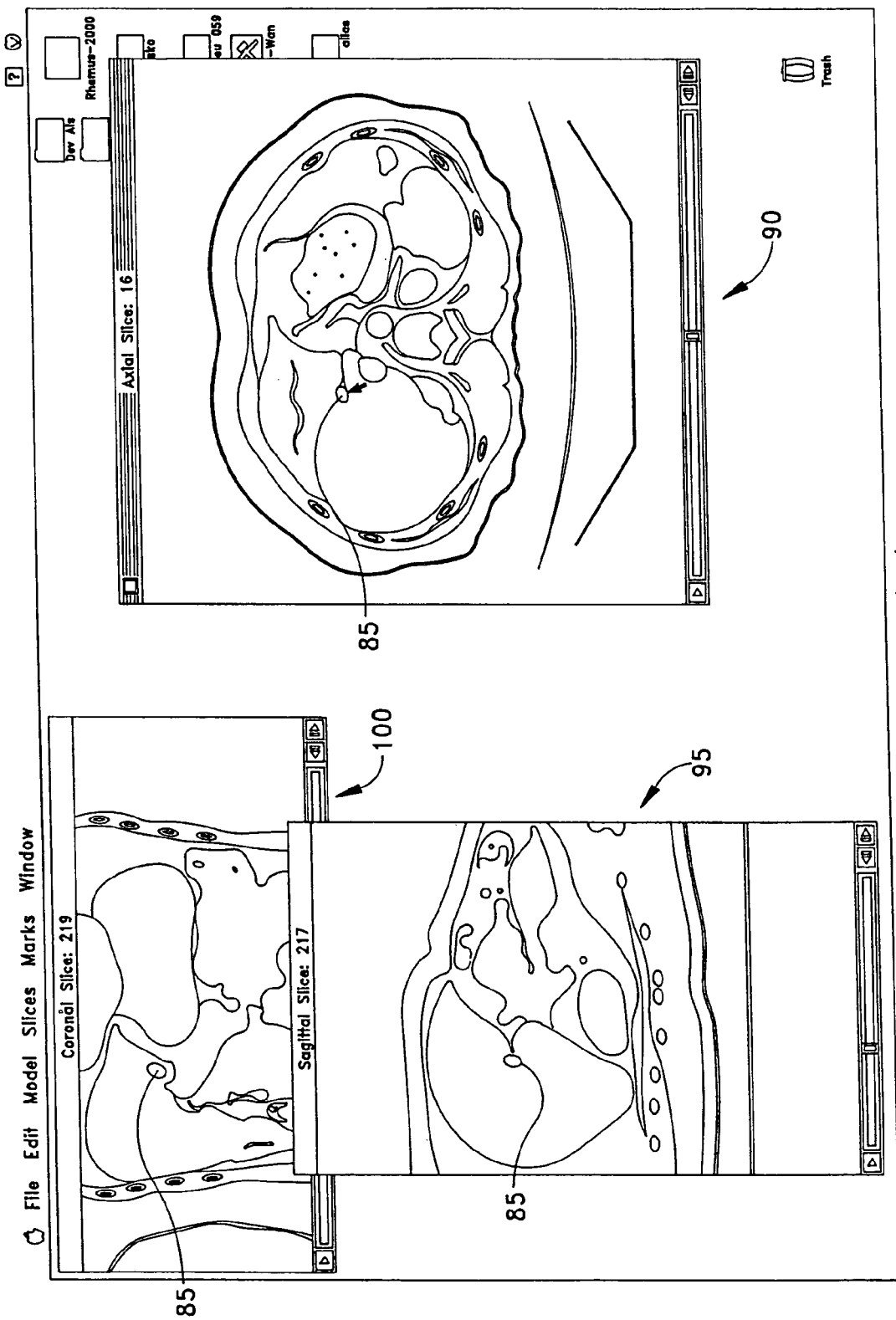
FIG. 14 illustrates three different images being displayed on a computer screen at the same time, with a marker being incorporated into each of the images.

In connection with the present invention, the sagittal and coronal 2-D slice image data may be stored with the axial slice image data in second section 40 of data storage device or medium 30. Preferably these sagittal and coronal slice images are stored in exactly the same data format as the 2-D axial slice images, whereby they may be easily accessed by computer 50 and displayed on display 60 in the same manner as has been previously discussed in connection with axial 2-D slice images. As a result, axial, sagittal and coronal 2-D slice images can be displayed on display 60, either individually or simultaneously in separate windows, in the manner shown in FIG. 14. Furthermore, when generating a composite image of the sort shown in FIG. 12 (i.e., an image generated from both the 3-D computer model contained in first section 35 of data storage device or medium 30 and a 2-D slice image contained in second section 40 of data storage device or medium 30), the composite image can be created using axial, sagittal or coronal 2-D slice images, as preferred.

It is also to be appreciated that the system of the present invention is also configured so as to generate and utilize oblique 2-D slice image data in place of the axial, sagittal and coronal slice image data described above. More particularly, computer 50 is programmed so that a physician can use input devices 55 to specify the location of the oblique 2-D slice image desired, and then computer 50 generates that 2-D slice image from the volumetric data set present in second section 40 of data storage device or medium 30 (i.e., from the collection of 2-D slice images contained in second section 40 of data storage device or medium 30).

It should be appreciated that data storage device or medium 30 can comprise conventional storage media (e.g., a hard disk, a CD ROM, a tape cartridge, etc.), which can be located either on-site or at a remote location linked via appropriate data transfer means.

Markers and Margins

In a further aspect of the present invention, computer 50 is programmed so that a physician can display a specific 2-D slice image in a window opened on display 60, place a marker into that specific 2-D slice image using a mouse or other input device 55, and then have that marker automatically incorporated into both (i) the 3-D computer model contained in first section 35 of data storage device or medium 30, and (ii) any appropriate 2-D slice image data contained in second section 40 of data storage device or medium 30. As a result, when images are thereafter generated from the 3-D computer model contained in first section 35 of data storage device or medium 30, and/or from the 2-D slice image data contained in second section 40 of data storage device or medium 30, these subsequent images will automatically display the marker where appropriate. See, for example, FIG. 14, which shows one such marker 85 displayed in its appropriate location in each of the three displayed 2-D slice images, i.e., in axial slice image 90, sagittal slice image 95, and coronal slice image 100. It is to be appreciated that it is also possible for marker 85 to be displayed where appropriate in an image generated from the 3-D computer model contained in first section 35 of data storage device or medium 30; see, for example, FIG. 15, which shows such a marker 85 being displayed in the image.

Figure 15:
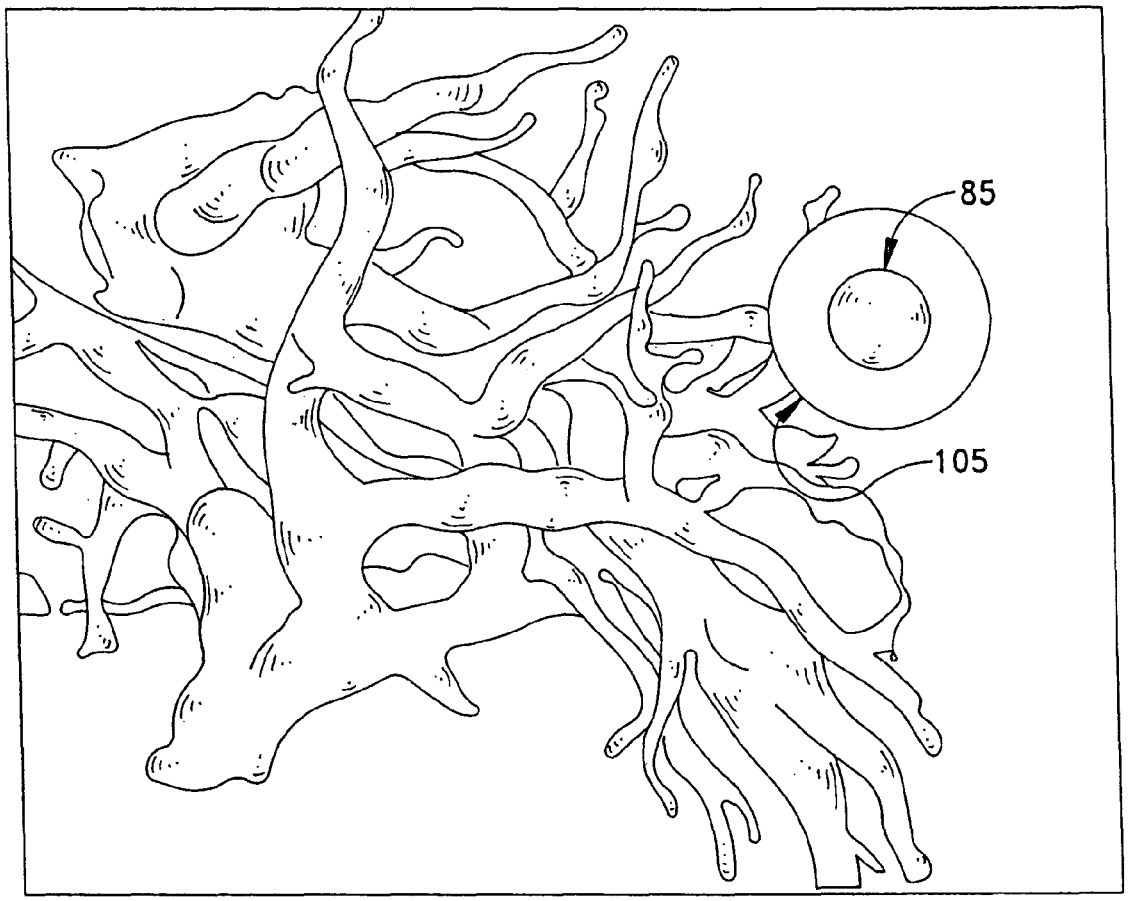
FIG. 15 illustrates a marker shown in an image generated from the 3-D computer model, with the marker being surrounded by a margin of pre-determined size.

In yet another aspect of the present invention, computer 50 is programmed so that a physician can generate a "margin" of some predetermined size around such a marker. Thus, for example, in FIG. 15, a margin 105 has been placed around marker 85. In this respect it is to be appreciated that margin 105 will appear as a 3-dimensional spherical shape around marker 85, just as marker 85 appears as a 3-dimensional shape, since the view of FIG. 15 is generated from the 3-D computer model contained in first section 35 of data storage device or medium 30. Alternatively, where marker 85 and margin 105 are displayed in the context of 2-D slice images, the marker and margin will appear as simple circles. Margin 105 can be used by a physician to determine certain spatial relationships in the context of the anatomical structure being displayed on the computer.

Peripheral Highlighting

Figure 16:
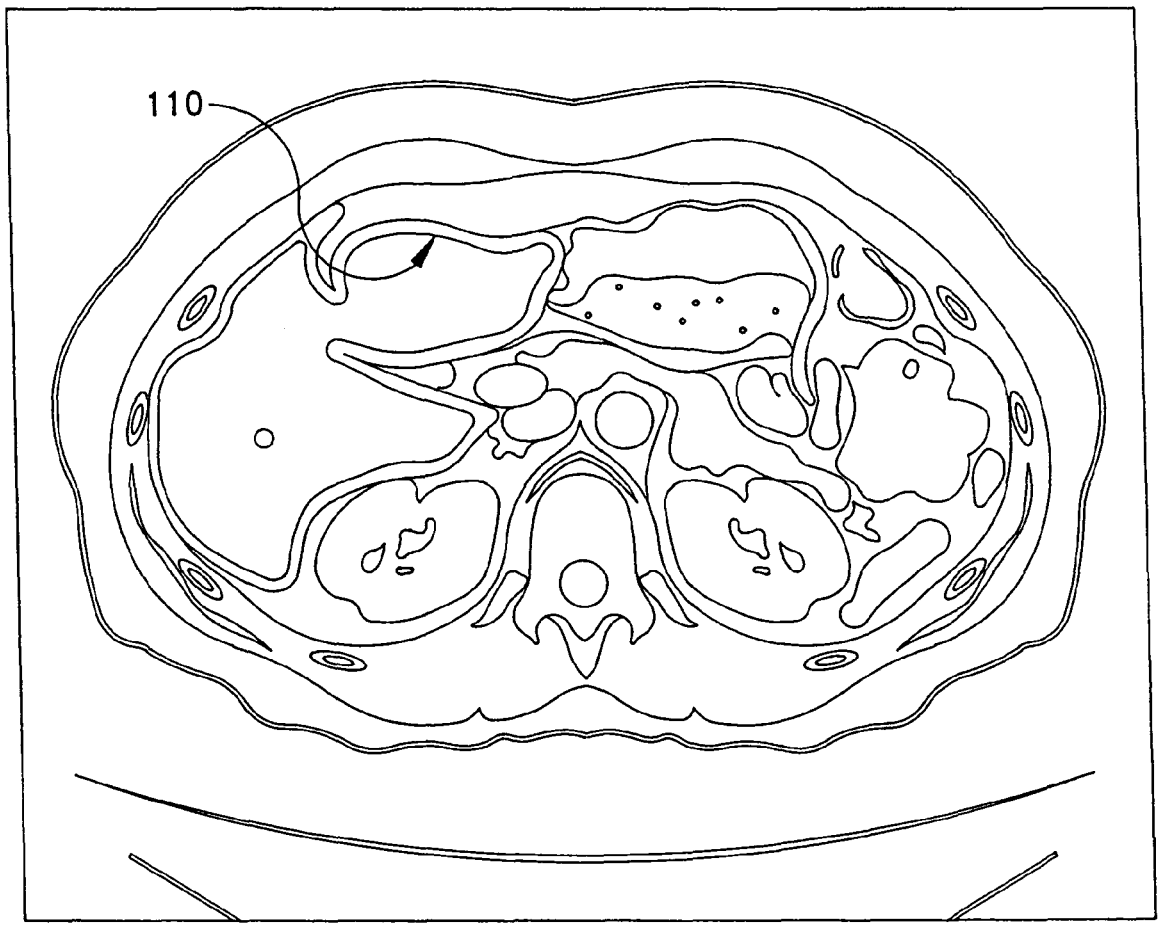
FIG. 16 illustrates a 2-D slice image, wherein the periphery of an object has been automatically highlighted by the system.

It is also to be appreciated that, inasmuch as the 3-D computer model contained in first section 35 of data storage device or medium 30 constitutes a plurality of software objects defined by polygonal surface models, it is possible to identify the periphery of any such objects in any corresponding 2-D slice image data contained in second section 40 of data storage device or medium 30. As a result, it is possible to highlight the periphery of any such object in any 2-D slice images displayed on display 60. Thus, in another aspect of the invention, computer 50 is programmed so that a physician can select one or more anatomical structures using an input device 55, and the computer will then highlight the periphery of that structure in any corresponding 2-D slice images displayed on display 60. See, for example, FIG. 16, where a boundary 110 is shown outlining the periphery of an object 115 displayed in a 2-D slice image.

Other Modifications of the Basic System

Furthermore, while in the foregoing description the present invention has been described in the context of an anatomical visualization system being used by a physician, it is also to be appreciated that the system could be used in conjunction with inanimate objects being viewed by a non-physician, e.g., the system could be used to visualize substantially any object for which a 3-D computer model and a collection of 2-D slice image data can be assembled.

It is also anticipated that one might replace the polygonal surface model discussed above with some other type of surface model. Thus, as used herein, the term "surface model" is intended to include polygonal surface models, parametric surface models such as B-spline surface models, quadralateral meshes, etc.

Centerline Calculations

In yet another form of the present invention, the visualization and measurement system may incorporate means for determining patient-specific anatomical dimensions using appropriate scanned 2-D image data.

For purposes of illustration but not limitation, this aspect of the present invention will be discussed in the context of measuring a patient's vascular structure in the region of the aortic/iliac branching. By way of further example, such measurement might be conducted in the course of repairing an aortic aneurysm through installation of a vascular prosthesis.

Figure 17:
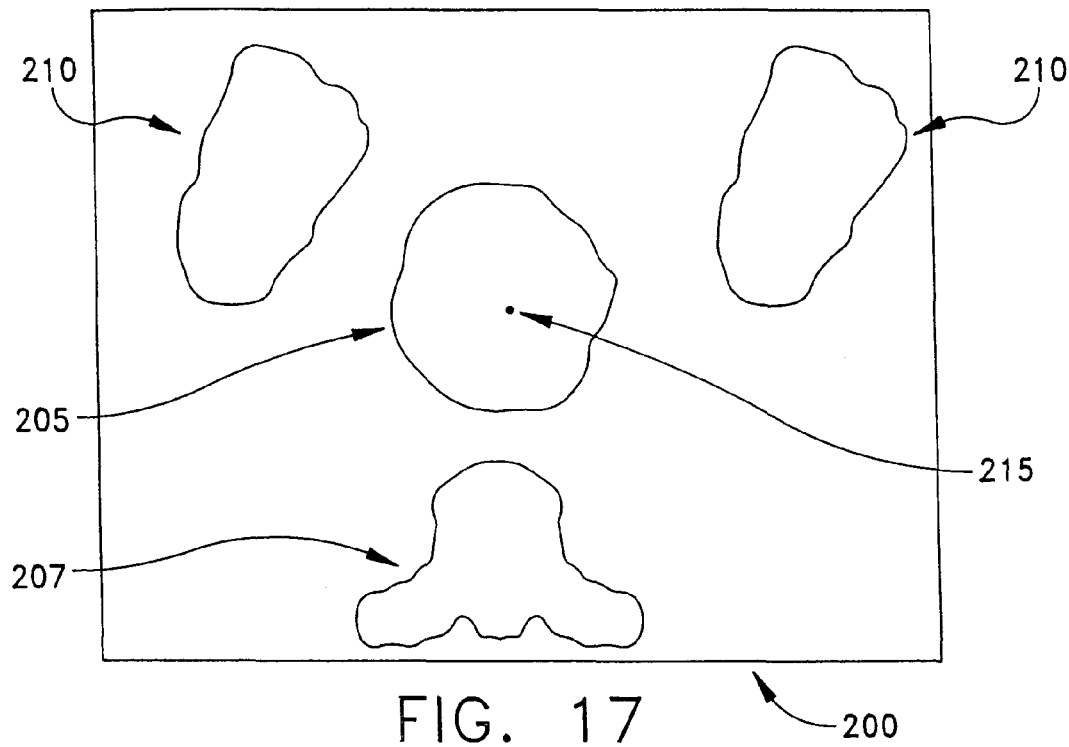
FIG. 17 is a schematic illustration showing various anatomical structures on a 2-D slice image, where that 2-D slice image has been taken axially through the abdomen of a patient, at a location above the aortic/iliac branching.
Figure 18:
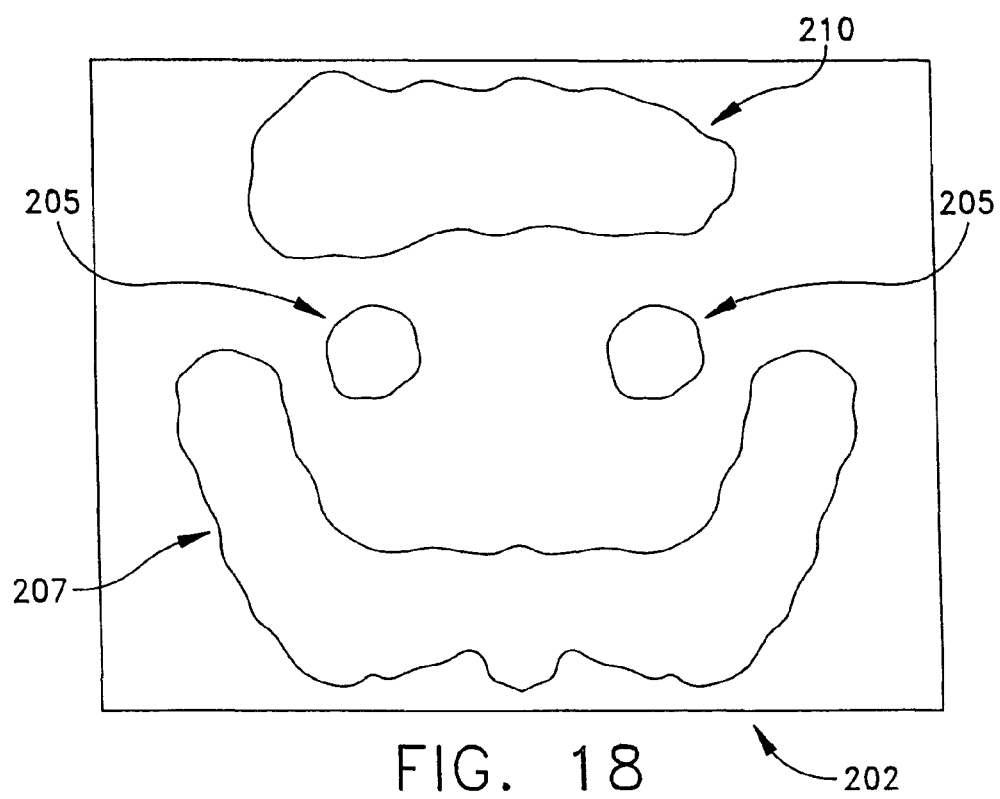
FIG. 18 is a schematic illustration showing various anatomical structures on another 2-D slice image, where that 2-D slice image has been taken through the abdomen of the same patient, at a location below the aortic/iliac branching.

More particularly, using the aforementioned scanning device 5, a set of 2-D slice images is first generated, where each 2-D slice image corresponds to a specific viewing plane or "slice" taken through the patient's body. As noted above, on these 2-D slice images, different types of tissue are typically represented by different image intensities. By way of example, FIG. 17 illustrates a 2-D slice image 200 taken through the abdomen of a patient, at a location above the aortic/iliac branching; FIG. 18 illustrates a 2-D slice image 202 taken through the abdomen of the same patient, at a location below the aortic/iliac branching. In these images, vascular tissue might be shown at 205, bone at 207, other tissue at 210, etc. An appropriate set of these 2-D slice images is assembled into a 3-D database so as to provide a volumetric data set corresponding to the anatomical structure of the patient. Referring back to the system illustrated in FIG. 6, the set of 2-D slice images making up this 3-D database might be stored in second section 40 of data storage device or medium 30. In this respect it is also to be appreciated that the 3-D database being referred to now is not the same as the 3-D computer model contained in first section 35 of data storage device or medium 30; rather, the 3-D database being referred to now is simply a volumetric data set made up of the series of 2-D slice images contained in second section 40 of data storage device or medium 30.

Next, using the appropriately programmed computer 50, the patient-specific volumetric data set (formed out of the collection of 2-D slice images contained in the 3-D database) is segmented so as to highlight the anatomical structure of interest.

This is preferably effected as follows. On the computer's display 60, the user is presented with 2-D slice images from the 3-D database, which images are preferably stored in second section 40 of data storage device or medium 30. As noted above, each of these 2-D images corresponds to a specific viewing plane or "slice" taken through the patient's body; or, stated slightly differently, each of these 2-D images essentially represents a plane cutting through the patient-specific volumetric data set contained in the 3-D database. As also discussed above, with each of these 2-D slice images, the different types of tissue will generally be represented by different image intensities. Using one or more of the input devices 55, e.g., a mouse, the user (who might or might not be a physician) selects a particular 2-D slice image for viewing on display 60, e.g., "slice image #155". The user then uses one or more of the input devices 55 to select one or more points located within the anatomical structure of interest. For convenience, such user-selected points can be referred to as "seeds". See, for example, FIG. 17, where a seed point 215 has been selected within the interior of vascular tissue 205 so as to identify blood. The user also uses one or more of the input devices 55 to specify a range of image intensities that appear to correspond to the anatomical structure of interest in the volumetric data set, e.g., blood within the interior of a blood vessel.

Figure 17A:
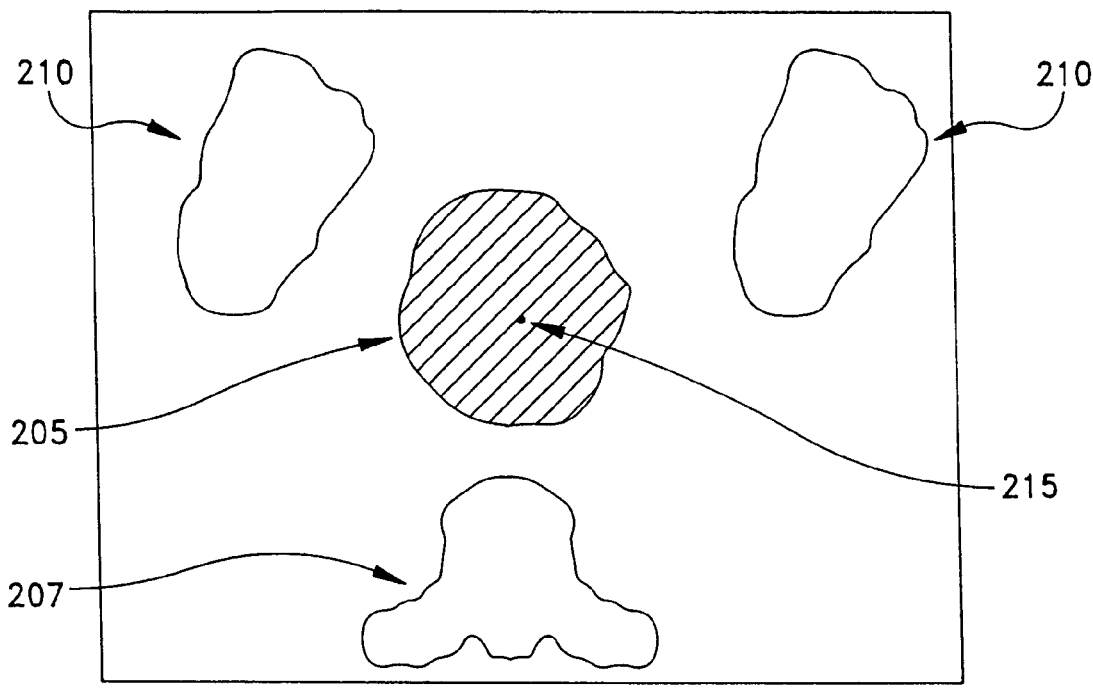
FIGS. 17A and 18A are schematic illustrations like those of FIGS. 17 and 18, respectively, except that segmentation has been performed in the 3-D database so as to highlight the patient's vascular structure.
Figure 18A:
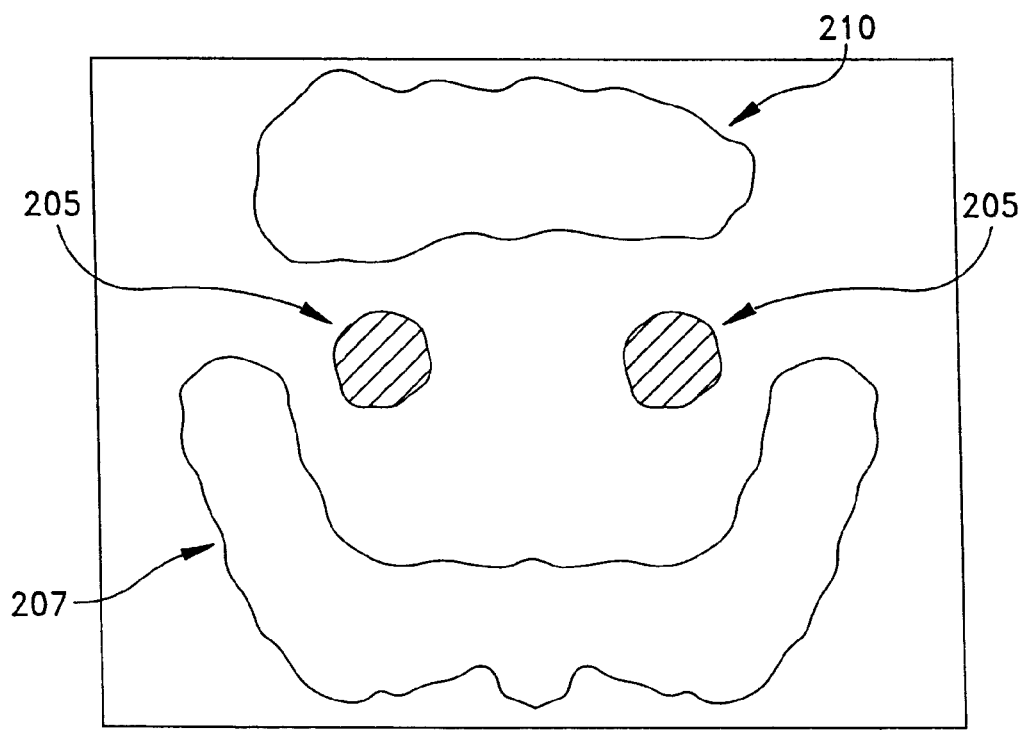

In accordance with the present invention, the appropriately programmed computer 50 then applies a segmentation algorithm of the sort well known in the art to segment out related structure within the patient-specific 3-D database. Preferably computer 50 is programmed to apply a 3-D connected component search through the volumetric data set contained in second section 40 of data storage device or medium 30 so as to determine the set of volumetric samples that are (i) within the range specified for blood, and which (ii) can be connected along a connected path back to one of the seeds, where each of the locations along the path is also within the range specified for blood. The result of this 3-D connected component search is a set of 3-D locations in the volumetric data set which correspond to blood flowing through the blood vessel. For the purposes of the present illustration, this set of 3-D locations can be characterized as the "blood region". The segmented anatomical structure (i.e., the blood in the blood region) can then be highlighted or otherwise identified on each of the 2-D slice images. See, for example, FIGS. 17A and 18A, where the segmented blood region in vascular tissue 205 has been cross-hatched to represent such highlighting.

Next, the branches in the segmented anatomical structure are identified. For example, and looking now at FIG. 19, in the present illustration dealing with vascular structure in the region of the aortic/iliac branching, the aorta and the two iliac branches would be separately identified.

This is done in the following manner. For each of the vessel segments that are part of the branching structure of interest, the user specifies a branch line in the volumetric data set that uniquely indicates that vessel segment. This is accomplished by using one or more of the input devices 55 to select, for each branch line, an appropriate "start" location on one of the 2-D slice images contained within second section 40 of data storage device or medium 30, and an appropriate "end" location on another one of the 2-D slice images contained within second section 40 of data storage device or medium 30. It should be appreciated that these branch lines do not need to cover the entire length of interest of the vessel and, in practice, will tend to stop somewhat short of the junction where various branches converge with one another. At the same time, however, for improved accuracy of modeling the branching structure, the branch lines should extend close to the bifurcation point.

For each of the vessel branches, the start and end locations are used to subdivide the blood region as follows: the region for that vessel branch is the set of locations within the blood region that are between the start plane and the end plane, where the start plane for each vessel branch is the 2-D image plane passing through the start location for the corresponding branch line, and the end plane for each vessel branch is the 2-D image plane passing through the end location for each vessel branch.

Figure 19:
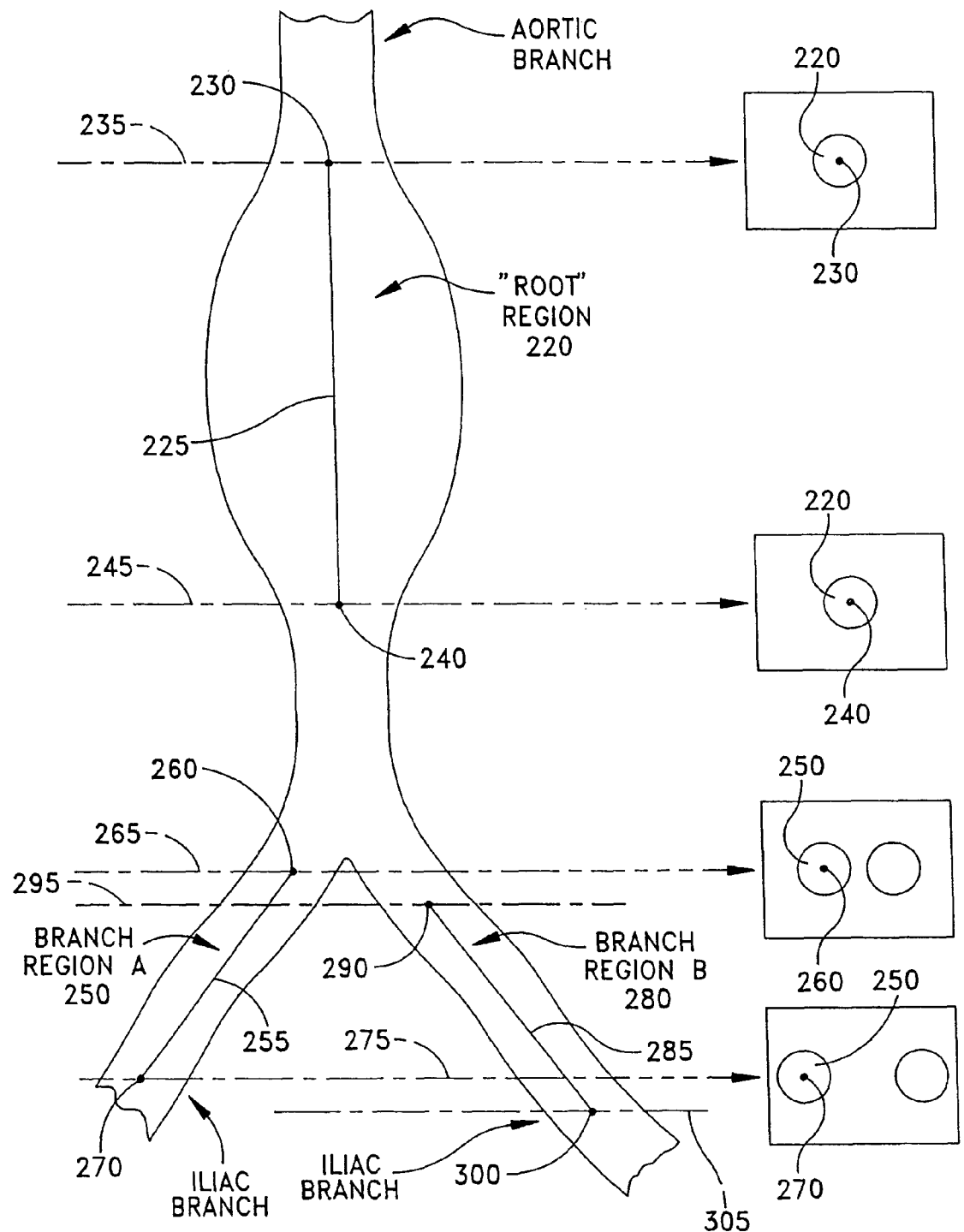
FIG. 19 is a schematic illustration showing that same patient's vascular structure in the region about the aortic/iliac branching, with branch lines having been specified for the patient's aorta and two iliac branches.

Although the invention could be used for a more complex branching structure through obvious extensions, it is useful to consider a vessel branch structure consisting of just three vessel segments coming together at a branch point, e.g., a vessel branch structure such as the aortic/iliac branching shown in FIG. 19. In this case, the user would designate one vessel region as the root region (e.g., the aortic region 220 defined by a branch line 225 having a start location 230 contained in a start plane 235, and an end location 240 contained in an end plane 245) and the other vessel regions as branch region A (e.g., the iliac region 250 defined by a branch line 255 having a start location 260 contained in a start plane 265, and an end location 270 contained in an end plane 275), and branch region B (e.g., the iliac region 280 defined by a branch line 285 having a start location 290 contained in a start plane 295, and an end location 300 contained in an end plane 305), respectively.

Figure 20:
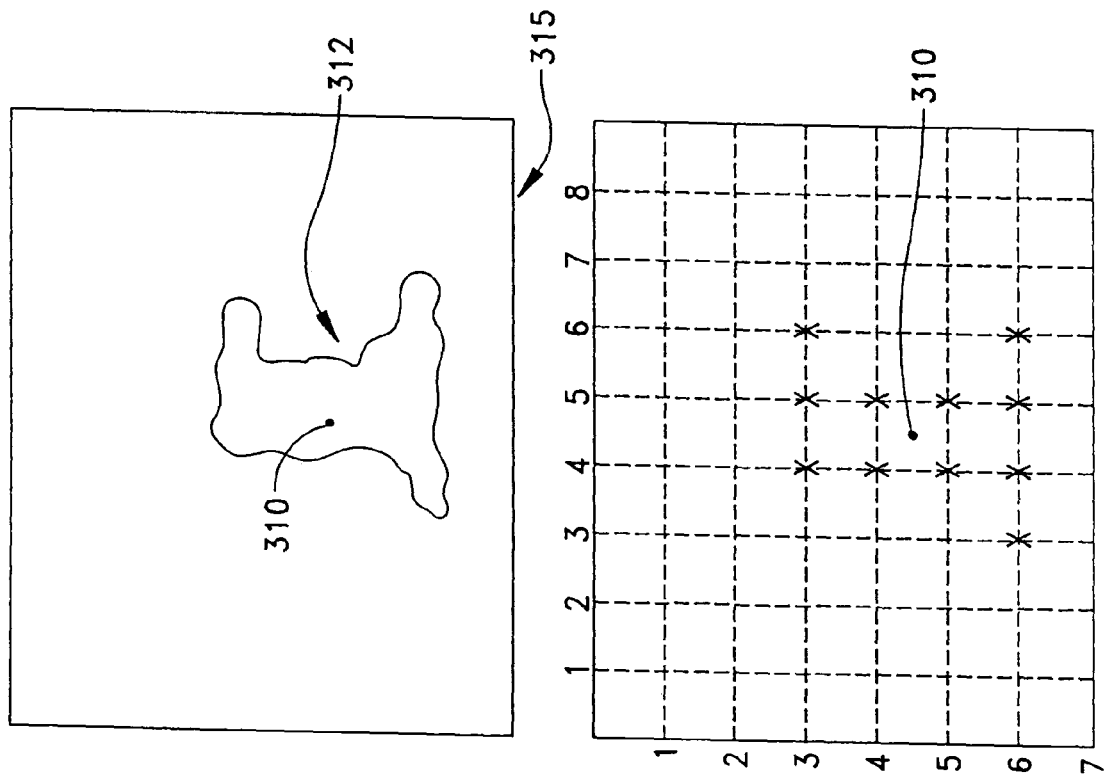
FIG. 20 is a schematic illustration showing how the centroid is calculated for the branch structure contained in a particular scanned 2-D image.

For each of the vessel regions determined in the previous step, a centroid path is then calculated. This is accomplished in the following manner. First, at intervals along the vessel line corresponding to the volumetric location of each of the original 2-D slice images contained in second section 40 of data storage device or medium 30, the centroid of the vessel region in that particular 2-D slice image is calculated. This is done by averaging the image coordinates of all locations in that 2-D slice image that are within the vessel region so as to yield a centroid point. See, for example, FIG. 20, which schematically illustrates the manner of calculating the centroid 310 for a representative vessel region 312 in a representative 2-D slice image 315.

Figure 21:
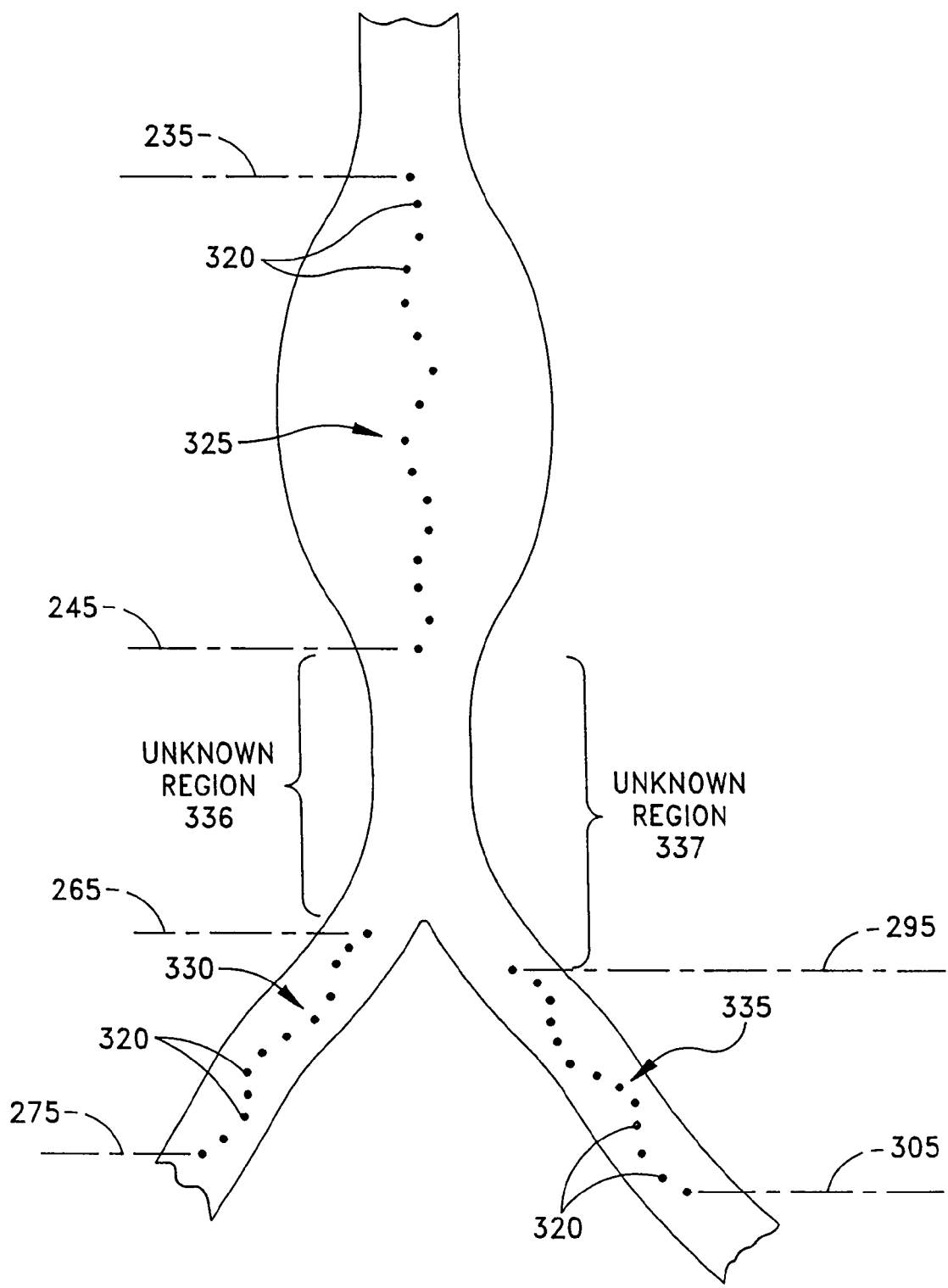
FIG. 21 is a schematic illustration showing the tortuous centroid path calculated for each of the respective branch lines shown in FIG. 19.

The centroid path for each vessel region is then established by the collective set of centroid points located along that vessel segment in three-dimensional space. The tortuous path corresponding to the root region is called the root centroid path and the tortuous paths corresponding to branch regions A and B are called branch centroid path A and branch centroid path B, respectively. See, for example, FIG. 21, which shows a plurality of centroids 320, a root centroid path generally indicated at 325, a branch centroid path A generally indicated at 330, and a branch centroid path B generally indicated at 335, all shown in the context of a vessel branch structure such as the aortic/iliac branching example discussed above. It is to be appreciated that no centroids will be defined in the "unknown" region 336 bounded by the end plane 245 and the start plane 265, and the "unknown" region 337 bounded by the end plane 245 and the start plane 295.

The system is programmed so that it will then apply a curve-fitting algorithm to the tortuous centroid paths determined above so as to supply estimated data for any portions of the anatomical structure which may lie between the aforementioned branch lines, and for "smoothing out" any noise that may occur in the system.

Figure 22:
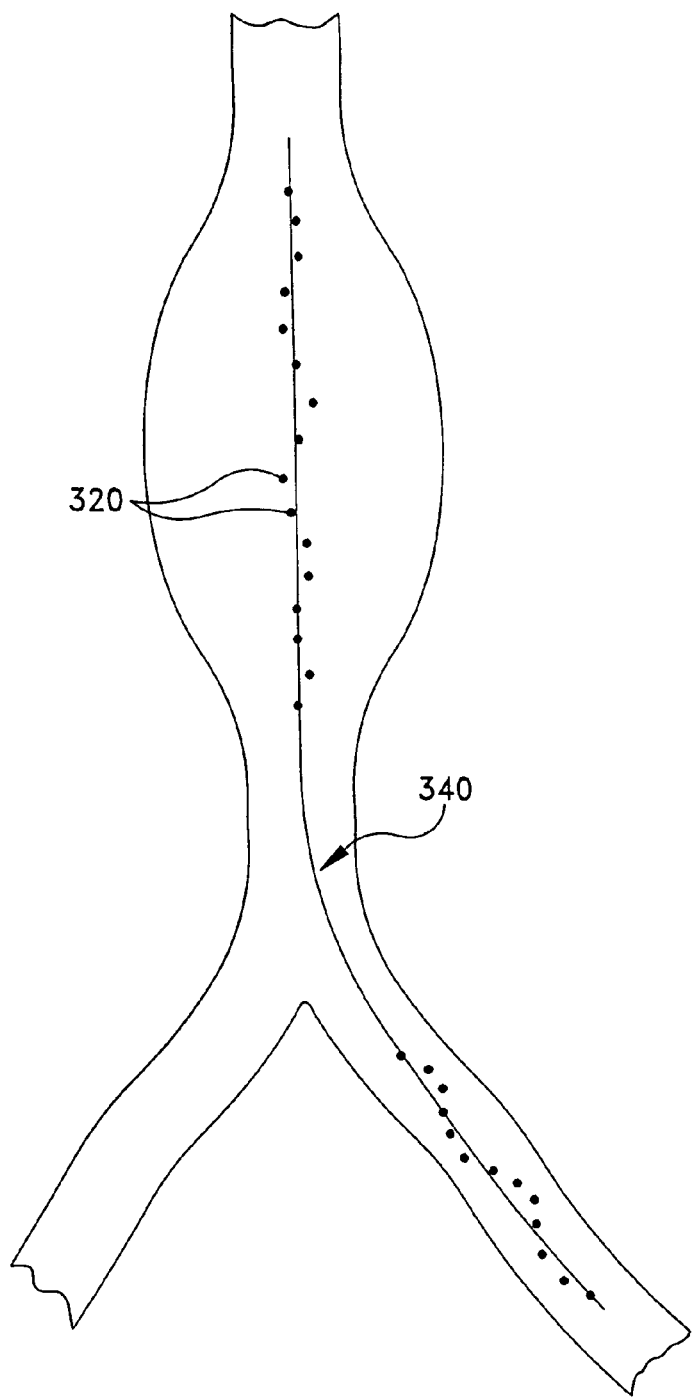
FIG. 22 is a schematic illustration showing the space curve determined by applying a curve-fitting algorithm to two of the centroid paths shown in FIG. 21, whereby the structure between the branch lines is filled out and the centroid data "smoothed" through a "best fit" interpolation technique.

This is preferably done through a spline fitting algorithm effected in the following manner. First, two new paths are created, by concatenating the points in the root centroid path 325 with the points in each of the two branch centroid paths 330 and 335, so as to create a path root-A and a path root-B. These two new paths are then used as the input to a spline fitting routine which selects the coefficients for a piecewise polynomial space curve that best approximates the points along the path in a least-squares sense. The number of pieces of the approximation and the order of polynomial may be varied by the user. The resulting curves may be called spline-root-A and spline-root-B. See, for example, FIG. 22, which illustrates the spline-root-B, generally indicated at 340.

Through numerical integration, the distance along the two splines (i.e., spline-root-A and spline-root-B) can then be calculated using standard, well-known techniques, and the result can be presented to the user. These calculations can be used for a variety of purposes, e.g., to help determine the appropriate size of a vascular prosthesis to be used in repairing an aneurysm at the aortic/iliac junction.

In addition, using well established mathematical techniques, at any point along the spline paths, a tangent vector and a perpendicular plane can be readily determined either by direct calculation or by definition in those cases where direct calculation would be undefined. By calculating the distance from the spline path to the points in the volumetric data set corresponding to the vessel branch region that are within an epsilon distance of the perpendicular plane, the shape of the vessel at that point can be determined, and the radius of a circle that best fits the cross-sectional area of the vessel at that point can also be readily calculated. Again, this result can be used to help determine that desired graft shape.

Figure 23:
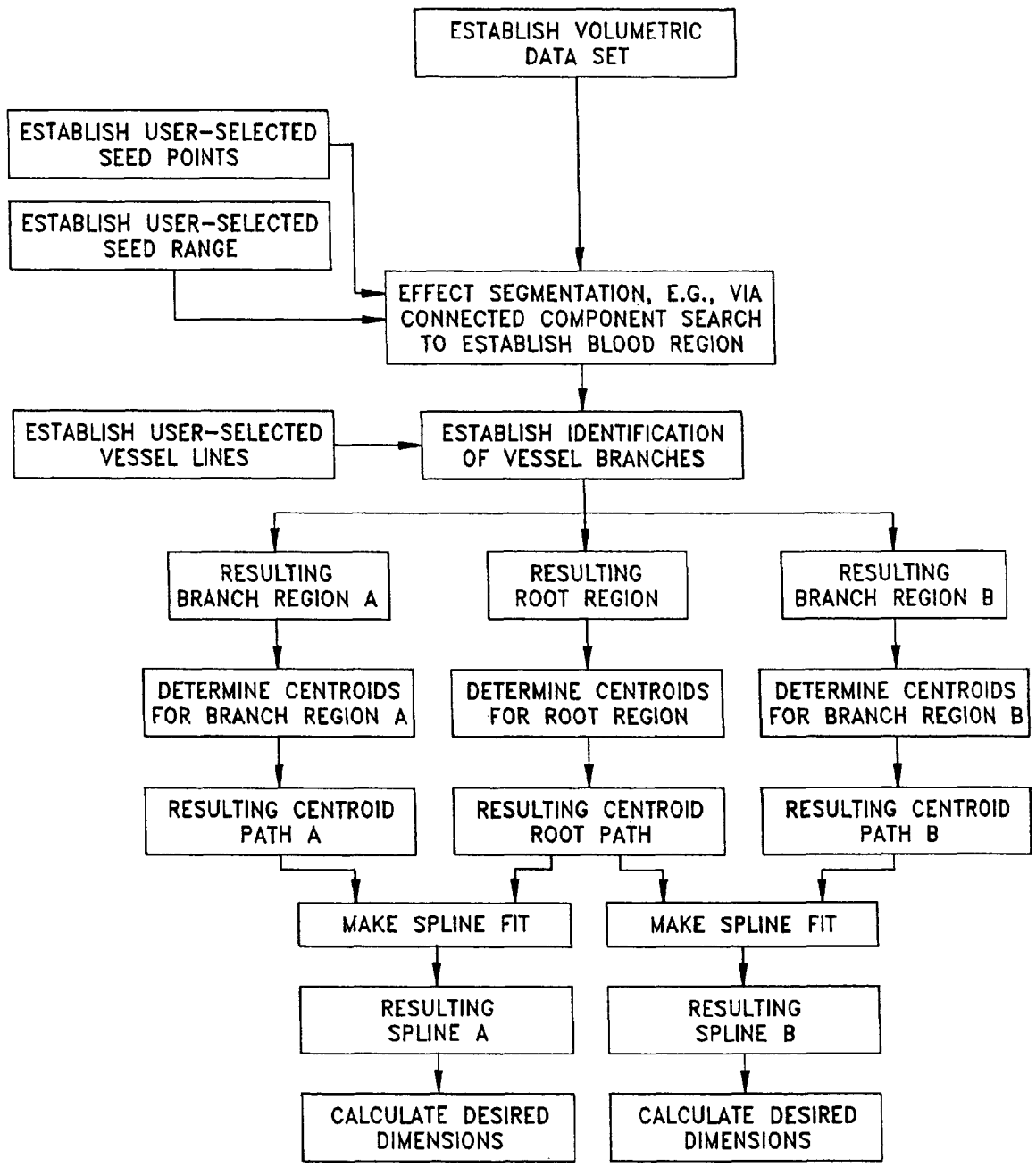
FIG. 23 is a flow chart illustrating how patient-specific anatomical dimensions can be determined from scanned 2-D image data in accordance with the present invention.

FIG. 23 is a flow chart illustrating how patient-specific anatomical dimensions can be determined from scanned 2-D data in accordance with the present invention.

In addition to the foregoing, it is possible to use the centerline derived above to generate additional views for the observer, and/or to make further anatomical calculations and measurements.

Oblique Slices Derived from the Centerline

Among other things, it is possible to use the centerline derived above to construct a series of oblique slices through the volumetric data set (which volumetric data set is formed out of the assembled scanned 2-D slice images contained in second section 40 of data storage device or medium 30) such that the reconstructed oblique slices are disposed perpendicular to the centerline.

More particularly, oblique slices per se are generally well known in the art, to the extent that such oblique slices are arbitrary planar resamplings of the volumetric data set. However, the utility of these arbitrary oblique slices is limited for many applications, since there is no explicit, well-defined relationship between their position and anatomical structures of interest. By way of example, in the case of blood vessels, oblique slices taken perpendicular to the length of the blood vessel are of particular importance to the physician. However, when generating oblique slices using traditional techniques (e.g., by pointing with an input device 55 while viewing the display 60), it is very difficult for the physician to specify the oblique slice which is truly perpendicular to the blood vessel at a specified point. This problem is avoided with the present invention, which utilizes the centerline as derived above to generate the set of oblique slices lying perpendicular to the blood vessel. This set of oblique slices derived from the centerline is preferably stored in a fourth section 400 of data storage device or medium 30 (FIGS. 5 and 6).

In general, one way to think about generating any oblique slice is to consider a four-sided polygon that is placed in the space defined by the volumetric data set. This polygon is then scan converted to resample the axial images so as to generate the oblique slice desired. As used herein, the term "scan converted" is intended to refer to the well-known techniques of subdividing a polygon into regularly spaced intervals on a rectangular grid.

Figure 24:
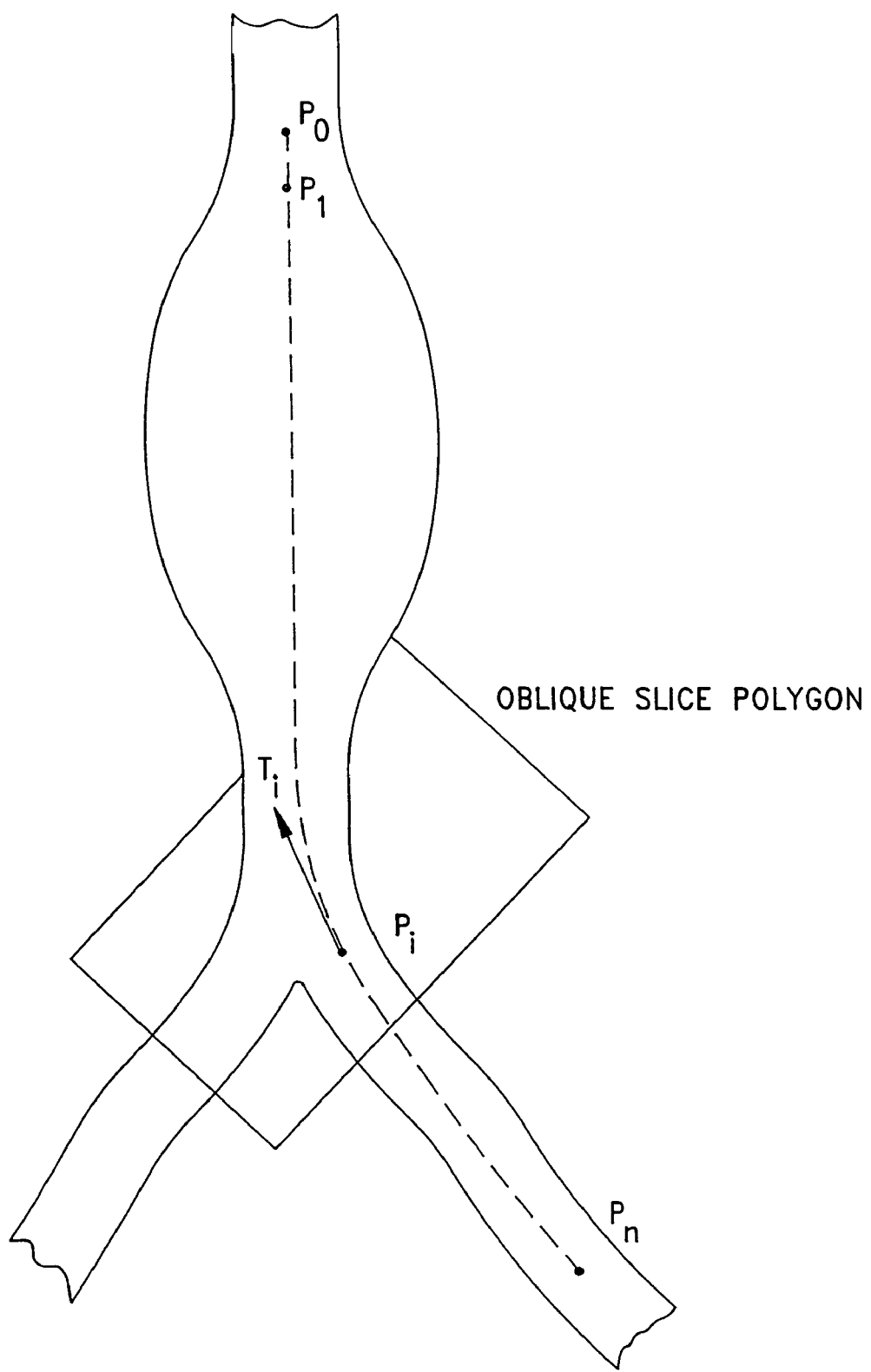
FIG. 24 is a schematic view showing an oblique slice polygon disposed perpendicular to the centerline of a blood vessel.

In the present invention a programmable computer is used to generate the specific set of oblique slices that is defined by the centerline derived above. This is accomplished as follows. First, the centerline is divided into n increments. This can be done with points $P_0, P_1, \ldots, P_n$, as shown in FIG. 24. A line $T_i$ is then derived for each of the points $P_i$, where $T_i$ is the tangent line at that point $P_i$. Finally a series of oblique slices are produced by constructing a series of four-sided polygons, each of which is centered at $P_i$ and normal to $T_i$. The locations of the corners of the polygon are selected such that the resulting image orientation is as close as possible to a pre-selected image orientation (e.g., axial). These four-sided polygons are then scan converted as described above so as to provide the set of oblique slice images lying perpendicular to the centerline. As noted above, this set of oblique slice images is stored in fourth section 400 of data storage device or medium 30. At the same time, the corner locations of each four-sided polygon associated with each oblique slice image is also stored in fourth section 400 of data storage device or medium 30, whereby the precise location of each oblique slice image within the volumetric data set is established.

As a result of the foregoing, the oblique slice images stored in fourth section 400 of data storage device or medium 30 is available to be accessed by computer 50 in exactly the same manner as the 2-D axial slice images stored in second section 40 of data storage device or medium 30.

Furthermore, once the aforementioned oblique slices have been derived from the centerline, these oblique slices can then be used for a variety of additional purposes.

Measuring Diameters Along the Centerline

As noted above, the oblique slice images derived from the centerline can be accessed by computer 50 from fourth section 400 of data storage device or medium 30. The physician can then use input devices 55 to instruct computer 50 to access the oblique slice at a particular location along the blood vessel and measure the diameter of the same. In particular, the physician can use input devices 55 to access the particular oblique slice desired and then lay down two diametrically-opposed marks so as to define the diameter of the blood vessel; the computer is adapted in ways well known in the art to then calculate the distance between the two marks. In this respect it should be appreciated that since the aforementioned oblique slice images are, by definition, taken perpendicular to the blood vessel at each point along the blood vessel, the blood vessel diameters so measured will tend be much more accurate than diameters calculated solely off axial slice images, and/or off coronal and/or sagittal and/or "standard", non-centerline-derived oblique slice images.

Measuring Distances with a Cumulative Sum Table

It has also been found that it can be advantageous to store the incremental distances between the centerline points $P_1, P_2, \ldots, P_n$ in a cumulative sum table in which the first entry, $C_0$, is 0; the second entry, $C_1$, is the distance between $P_1$ and $P_0$ (i.e., $C_1 = P_1 - P_0$); the third entry $C_2 = C_1 + (P_2 - P_1)$; etc. Thus, the centerline distance between any two points $P_i$ and $P_j$ is simply $D_{ij} = C_i - C_j$.

Figures 25, 26:
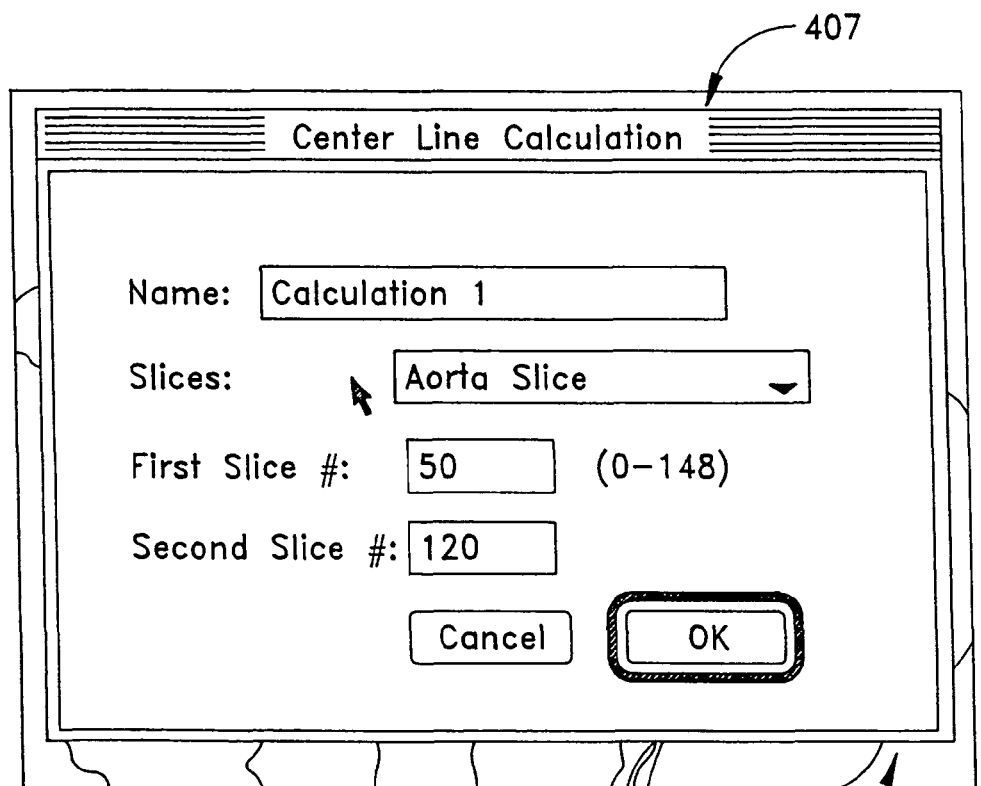
FIG. 25 is a cumulative sum table for calculating lengths along an anatomical structure.
FIG. 26 illustrates a centerline length calculation dialogue box drawn to a window in a display.

In the present invention, the cumulative sum table can be of the sort shown in FIG. 25. This cumulative sum table is preferably stored in a fifth section 405 of data storage device or medium 30. Computer 50 is also programmed so that the user interface presents a centerline length calculation dialogue box 407 (FIG. 26) to the physician on display 60, by which the physician can specify (using input devices 55) two oblique slice images which are the end points of the length which is to be determined. Computer 50 is programmed so that it will then determine the length between the two chosen oblique slices by calculating the difference in their positions from the cumulative sum table.

Figure 27:
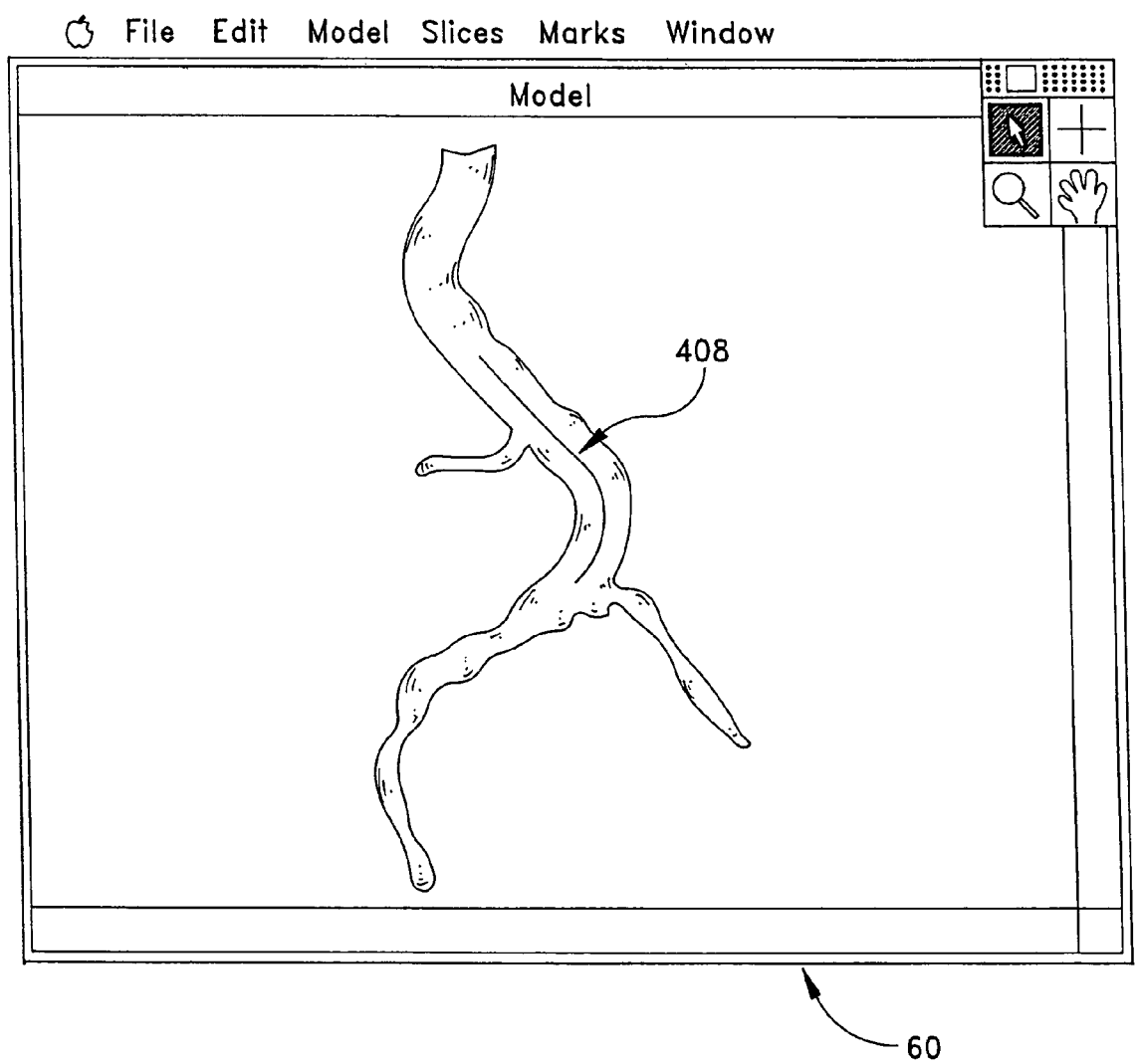
FIG. 27 illustrates a. 3-D graphical icon which has been inserted into the 3-D model and which is visible on the display so as to show the portion of the centerline which has been specified by the physician for a length calculation.

Computer 50 is also programmed so that a 3-D graphical icon 408 (FIG. 27) is inserted into the 3-D model contained in first section 35 of data storage device or medium 30. This icon represents the portion of the vessel centerline which has been specified by the physician via the two oblique slice images which represent the length end points.

Calculating Volumes Using a Cumulative Sum Table

A cumulative sum table can also be used to calculate volumes with respect to an anatomical structure, in much the same way that a cumulative sum table can be used to calculate lengths along an anatomical structure. However, incremental slice volumes are more appropriately calculated in the axial direction rather than in the oblique slice direction. This is because the axial slices all lie parallel to one another, whereas the oblique slices (since they are generated from the centerline) do not.

Figures 28, 29:
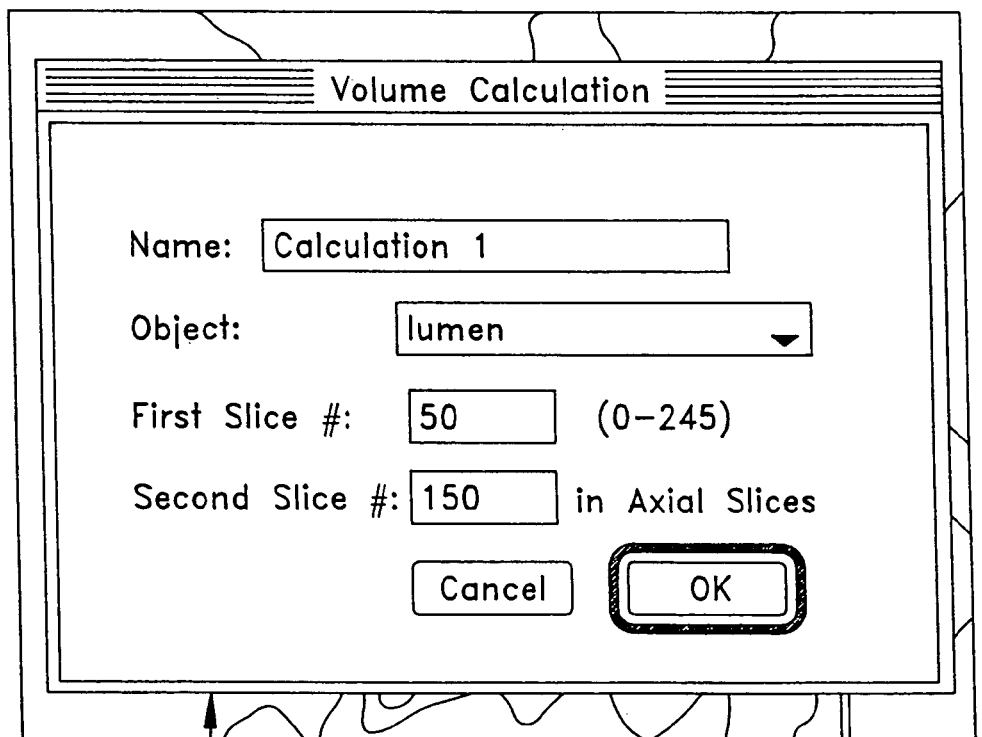
FIG. 28 is a cumulative sum table for calculating volumes with respect to an anatomical structure.
FIG. 29 illustrates a volume calculation dialogue box drawn to a window in a display.
Figure 30:
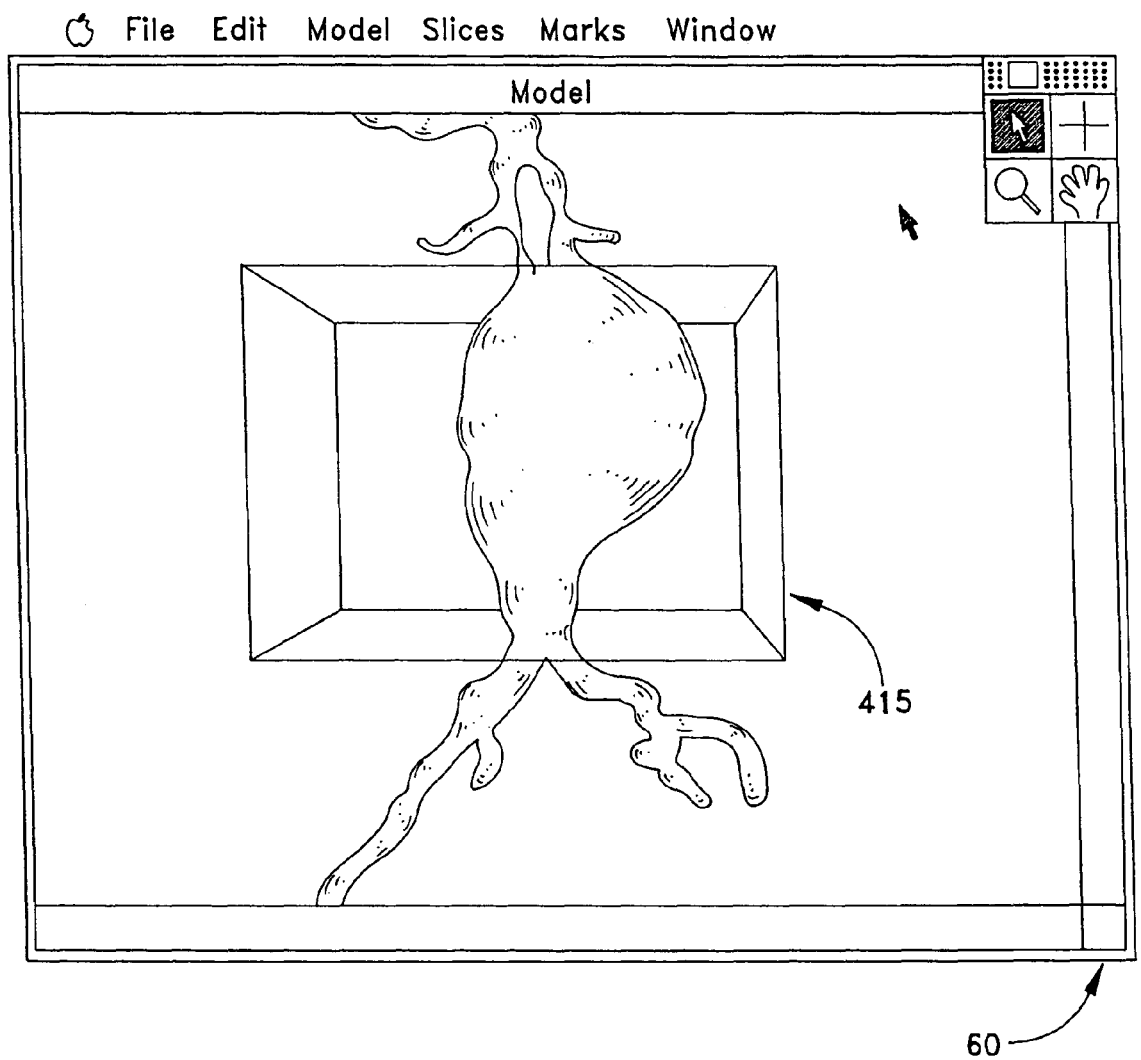
FIG. 30 illustrates a 3-D graphical icon which has been inserted into the 3-D model and which is visible on the display so as to show the volume which has been specified by the physician using the volume calculation dialogue box.

To this end, a computer is used to calculate the volume of each axial slice, $V_i$, by (1) determining the number of pixels in the segmented region of that axial slice, (2) scaling by the appropriate pixel-to-length factor, and then (3) multiplying by the slice thickness. A cumulative sum table is then generated, where the first entry, $C_0$, is $V_0$; the second entry, $C_1 = C_0 + V_1$; the third entry $C_2 = C_1 + V_2$; etc. In the present invention, this cumulative sum table can be of the sort shown in FIG. 28. This cumulative sum table is stored in sixth section 410 of data storage device or medium 30. Computer 50 is also programmed so that the user interface presents a volume calculation dialogue box 412 (FIG. 29) to the physician on display 60 that allows the physician to conveniently specify two axial slices as the end points of the volume to be determined. Computer 50 then calculates the volume for the region specified, using the cumulative sum table. Computer 50 is also programmed so as to place a 3-D graphical icon 415 (FIG. 30) in the 3-D model contained in the first section 35 of data storage device or medium 30. This icon represents the volume specified by the physician using the volume calculation dialogue box.

Finite Element Analysis (FEA) of Blood Vessels and Post-Analysis Stress Visualization There are approximately 2.3 million patients in the United States alone with abdominal aortic aneurysms (AAA). Left untreated, aortic aneurysms can rupture, causing an estimated 15,000 deaths per year, making this disease the 15th leading cause of death in the United States. Patients with AAA are generally over 65 years of age; many have additional health conditions that make them poor candidates for surgical intervention. The high risk of treatment for many AAA patients makes assessing the risk of aneurysm rupture a critical issue in the evaluation of each patient.

Conventional indices of rupture risk, generally based on maximum aneurysm diameters (e.g., typically a 5 cm threshold), are widely understood to be unreliable, but to date there has been no superior alternative method.

The present invention provides an improved system for assessing AAA rupture risk based on arterial wall stress analysis.

Finite element analysis (FEA), employing a finite element method (FEM), is a mathematical technique which may be used to perform stress analysis of physical structures, including stress analysis of the aortic wall for patients with AAA disease. The calculated maximum wall stress has been shown to be, generally, a much better predictor of AAA rupture than the standard 5 cm diameter measure currently used to predict AAA rupture.

The present invention provides a novel system for performing FEM stress analysis for AAA pre-op cases based on the scan/segmentation/polygonal surface model ("mesh objects") systems described above, and the blood vessel measurement systems described above, which systems are incorporated in the Preview® products commercially available from Medical Metrx Solutions (MMS) of West Lebanon, N.H. Among other things, the present invention comprises technology for: (i) using the segmentation techniques to generate patient-specific mesh objects, (ii) conducting finite element stress analysis on those patient-specific mesh objects, and (iii) providing post-analysis stress visualization.

More particularly, in one preferred embodiment, the present invention comprises a system for: (i) segmentation merging, (ii) visceral vessel removal, (iii) mesh boundary delineation, (iv) FEM mesh construction, (v) stress anlysis post-processing and visualization, and (vi) blood pressure interpolation.

(i) Segmentation Merging

In accordance with the present invention, the starting point is generally source medical images, such as from a computerized tomography (CT) or magnetic resonance imaging (MRI) scanner, in which various anatomical structures can be identified. Such structures can include bloodflow lumen, calcified plaque, and thrombus and non-calcified plaque. In general, CT scanners work by passing X-rays systematically through a body, while MRI scanners rely on a radio sensitive effect caused by aligning all the water molecules within the body using super conducting magnets.

The aorta is the main artery that takes blood from the heart, through the abdomen, and into the lower part of the body. An aneurysm refers to a disease state in which the blood vessel wall becomes weakened and then "balloons" out in a characteristic way. An abdominal aortic aneurysm (AAA) refers to an abnormal, localized enlargement of the aorta below the renal arteries (which feed the kidneys) and above the iliac bifurcation (which feeds the legs). Such an aneurysm will typically continue to enlarge in size and, if left untreated, will commonly rupture and may consequently cause death. The precise cause of AAA is unknown, but is most commonly associated with atherosclerosis, hypertension and smoking.

Bloodflow refers to that part of the vessel anatomy in which blood is freely flowing. Thrombus is clotted blood that is very thick and viscous. Calcified plaque is a hard bone-like substance that forms within blood vessels and is a clear contributor to vessel stenosis.

Figure 31:
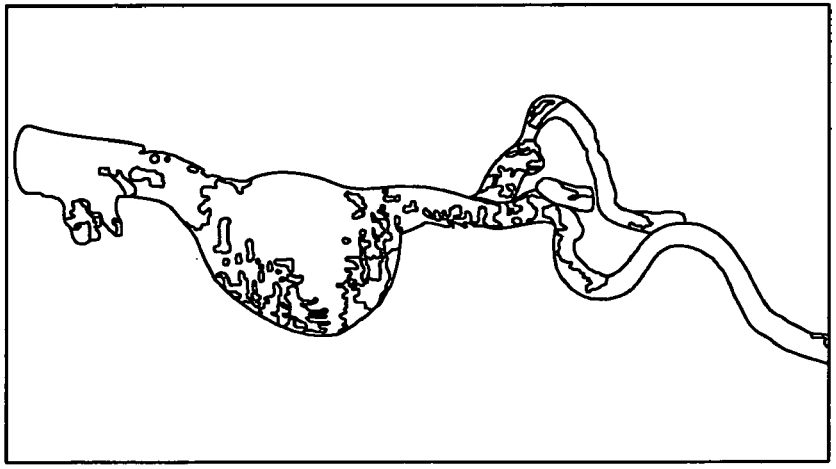
FIG. 31 illustrates a virtual model of an aortic aneurysm.

As described hereinabove, the reconstruction software (commercially available from Medical Metrx Solutions of West Lebanon, N.H.) is designed to optimize the accuracy of segmentation of multiple anatomical structures when used by trained technicians. Various segmentation tools allow for precise definition of bloodflow, thrombus/non-calcified plaque, calcium and other objects simultaneously during technician-guided processing of CT scan data. By way of example but not limitation, FIG. 31 illustrates MMS reconstruction of an actual abdominal aortic aneurysm. For clarity, regions where the blood is flowing are illustrated in red (dark gray in this black and white figure), regions of thrombus and plaque formation are illustrated in yellow (light gray), and regions of calcium are in white.

Figure 32:
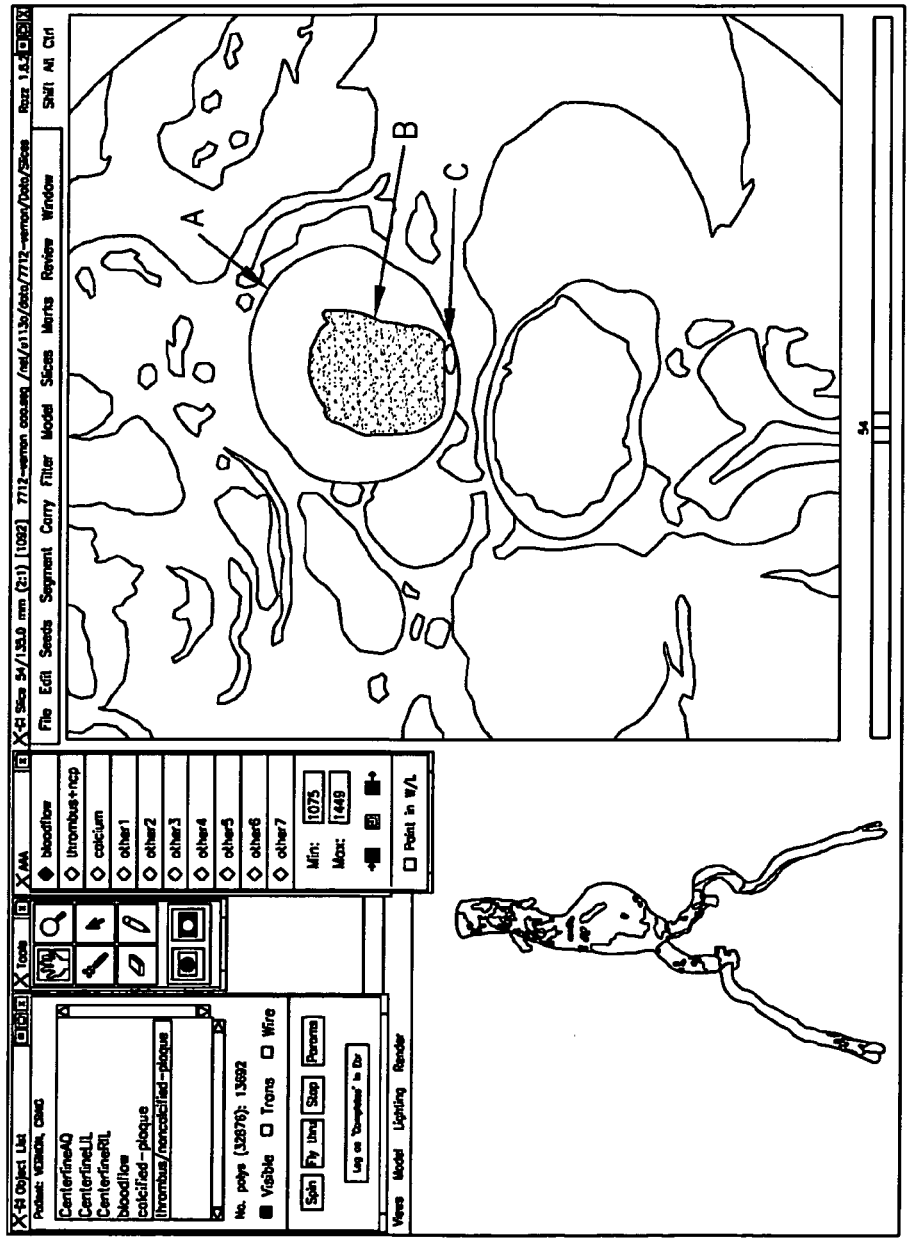
FIG. 32 is a screen display of the user interface for computer modeling software provided in accordance with the present invention.

FIG. 32 illustrates an example of a screen capture of the user interface for the MMS reconstruction software. In this illustration, segmentation A delineates thrombus, segmentation B delineates contrast-enhanced bloodflow, and segmentation C delineates calcium in the model.

In accordance with the present invention, the scan data is anatomically segmented on a slice-by-slice basis so as to generate anatomically segmented slices.

Next, in order to create a FEM mesh of the blood vessel, the individual segmented elements (e.g., free bloodflow, thrombus, calcified plaque, etc.) on each slice are merged back into a single collective element that represents the contents of the blood vessel. This operation can be accomplished with a logical "OR" operator. In one embodiment of the present invention, this may be performed automatically, using a simple tool which merges the appropriate segmented elements into the single collective element for each of the slices that contain the blood vessel.

Figure 33:
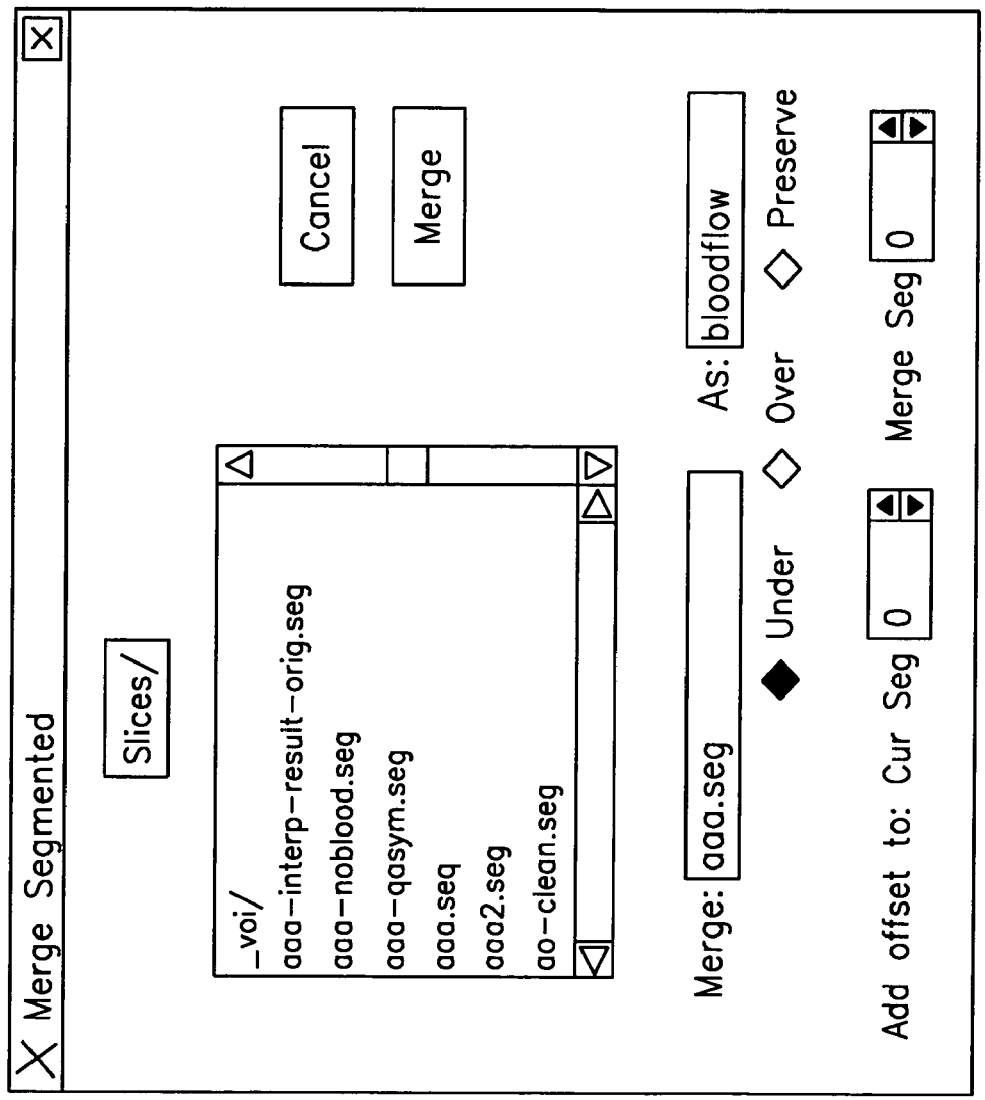
FIG. 33 is a screen display showing merging of the segmented scanned slices.

By way of example but not limitation, and looking now FIG. 33, a aaa.seg file may be specified to merge the selected segmented elements into the single collective "bloodflow" element. This merging may occur either under (i.e., in addition to) the existing segmentation, or on top (i.e., in place of) the existing segmentation. In addition, a spatial offset can be specified, but in general it is not required. Thus, at this point in the process, each slice will be segmented to include a collective bloodflow element which is representative of the entire contents (free bloodflow, thrombus, calcified plaque, etc.) of the blood vessel for that slice.

(ii) Visceral Vessel Removal

The computer model of the patient's anatomy frequently includes small visceral vessels extending off the main aorta flow. Such vessels may include, among others, the celiac, sma and renal arteries, and the ima and internal iliac arteries. These small visceral vessels typically constitute useful landmarks for the vascular surgeon when developing a surgical plan; however, they generally do not contribute significantly to the overall stress pattern found during FEM analysis, and they do add significantly to the processing time and solution size when building the computer model of the anatomy. Thus, it is generally useful to remove the segmentation elements for these vessels before the FEM mesh is constructed.

Such desired visceral vessel removal can be accomplished in a number of ways.

For example, since the number of slices containing the visceral vessels is relatively small, it can be acceptable to remove the unwanted segmentation elements manually. Thus, in the modeling workstation provided by MMS, this can be done with an "eraser" tool. In this system, by "Control clicking" with the "eraser" tool, whole regions (like the small renal island on the left side of FIG. 34A) can be removed with a single click.

Figure 34B:
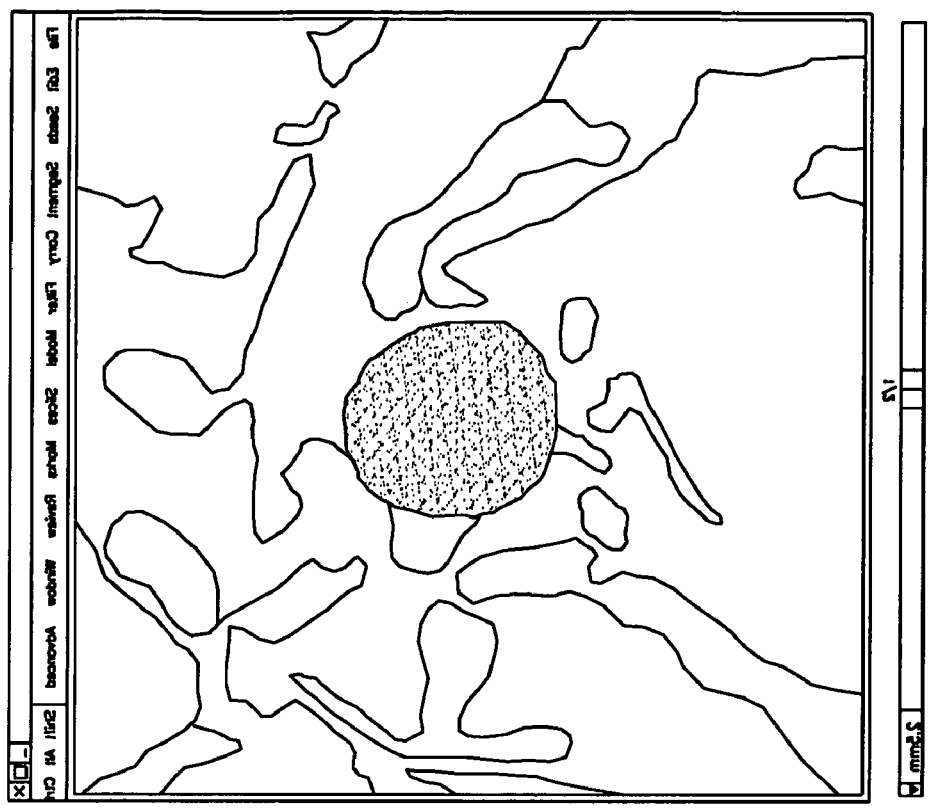
FIGS. 34A and 34B show slices of the segmented scan data.
Figure 34A:
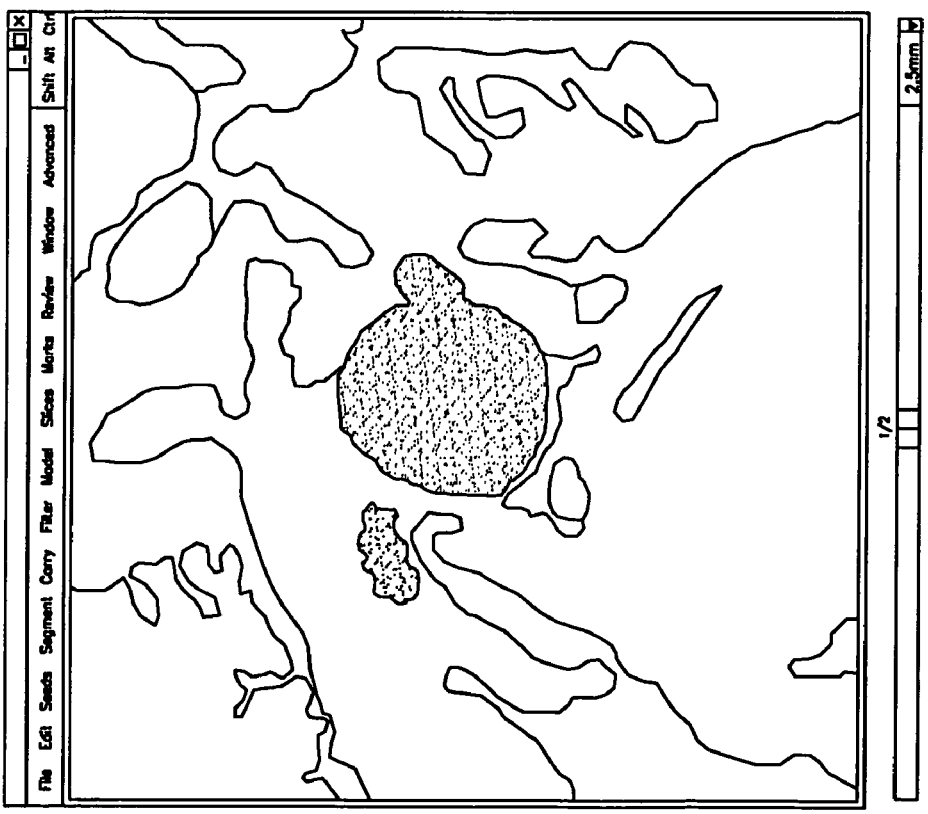

To accomplish similar results, more automatic means may be utilized. In FIGS. 34A and 34B, it is clear that the segmentation regions made from the "unwanted" visceral vessels is generally smaller than the aorta. Thus, a simple filter that erases all but the largest segmentation region may be beneficial. However, care must be taken in the regions below the iliac bifurcation, where multiple segmentation regions would be expected.

(iii) Mesh Boundary Delineation

Studies of the motion of the aorta during the cardiac cycle indicate that the attachment zone close to the renal arteries (the "high" attachment zone, which may be referred to, in the context of the heart, as the proximal attachment zone) and the attachment zones close to the iliac arteries (the "low" attachment zones, which may be referred to, in the context of the heart, as the distal attachment zones) are relatively fixed, while the intervening vessel can support some rigid body motion. Therefore, a simplification to an aneurysm model can be created in which the most proximal and most distal nodes are totally pinned (i.e., unable to translate). In order to be able to relax this restriction so as to better represent true anatomic constraints in the model, the present invention discloses a system which permits enough of the mesh below the iliac arteries to be preserved so that "springs" or "ties" can be added to the model. This is accomplished with the user interface illustrated in FIG. 35 and described below.

Figure 35:
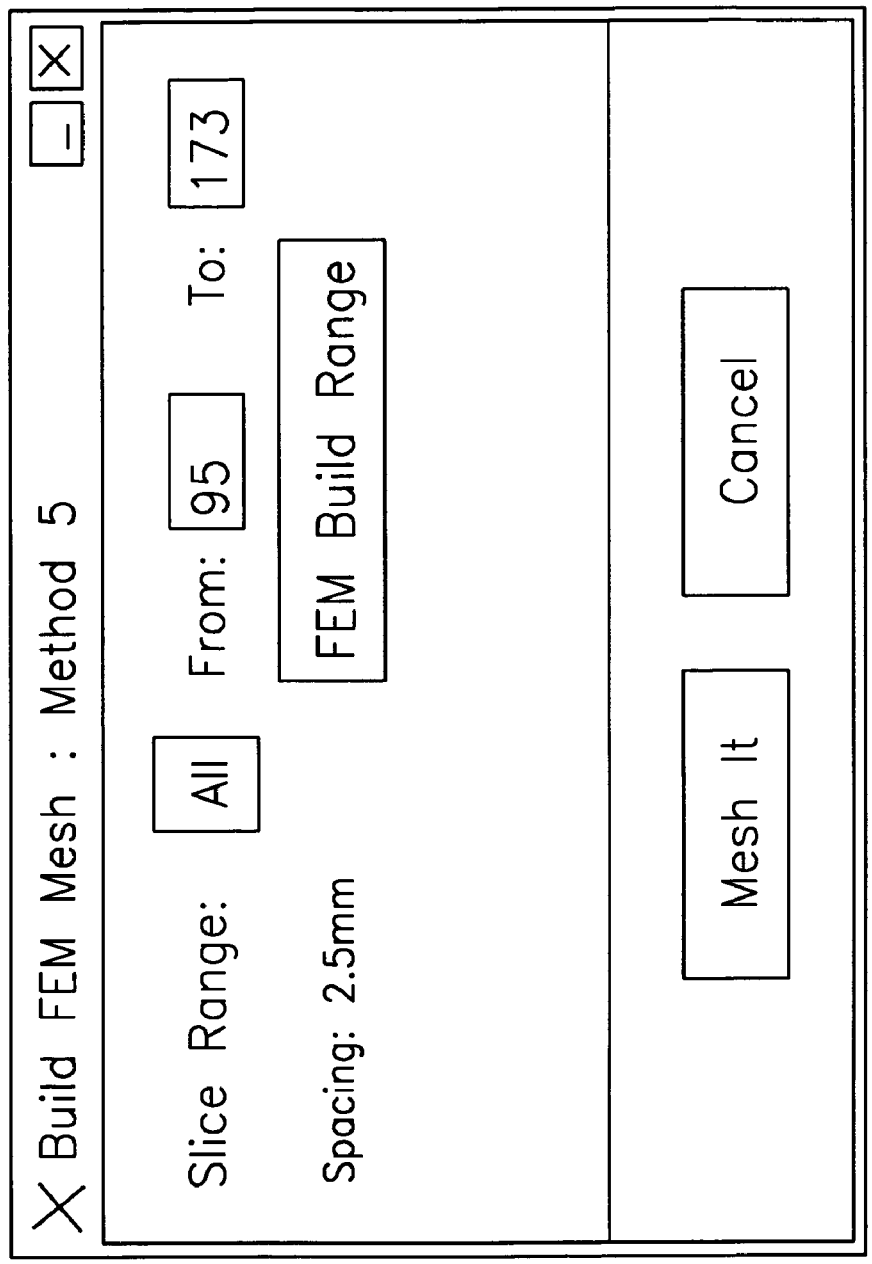
FIG. 35 is a screen display showing building of the FEM mesh.

First, the axial slice that intersects the lower part of the left or right iliac bifurcation is found via a "Control-click" on the 3D vessel model. The next step is to press the "FEM Build Range" button (FIG. 35). When the "FEM Build Range" button is pressed, the "From" field is filled with the slice number where the segmentation starts and the "To" field is filled with the frame number beyond the lowest bifurcation where both the left and right iliac branches become vertically aligned. In one preferred form of the system, such vertical alignment is determined by finding the angle between the centerline tangent and the z-axis (0 0 1). When this angle is less than a predetermined threshold (e.g., 45 degrees) for both the left and right iliac branches, then vertical alignment is considered achieved.

Figure 36:
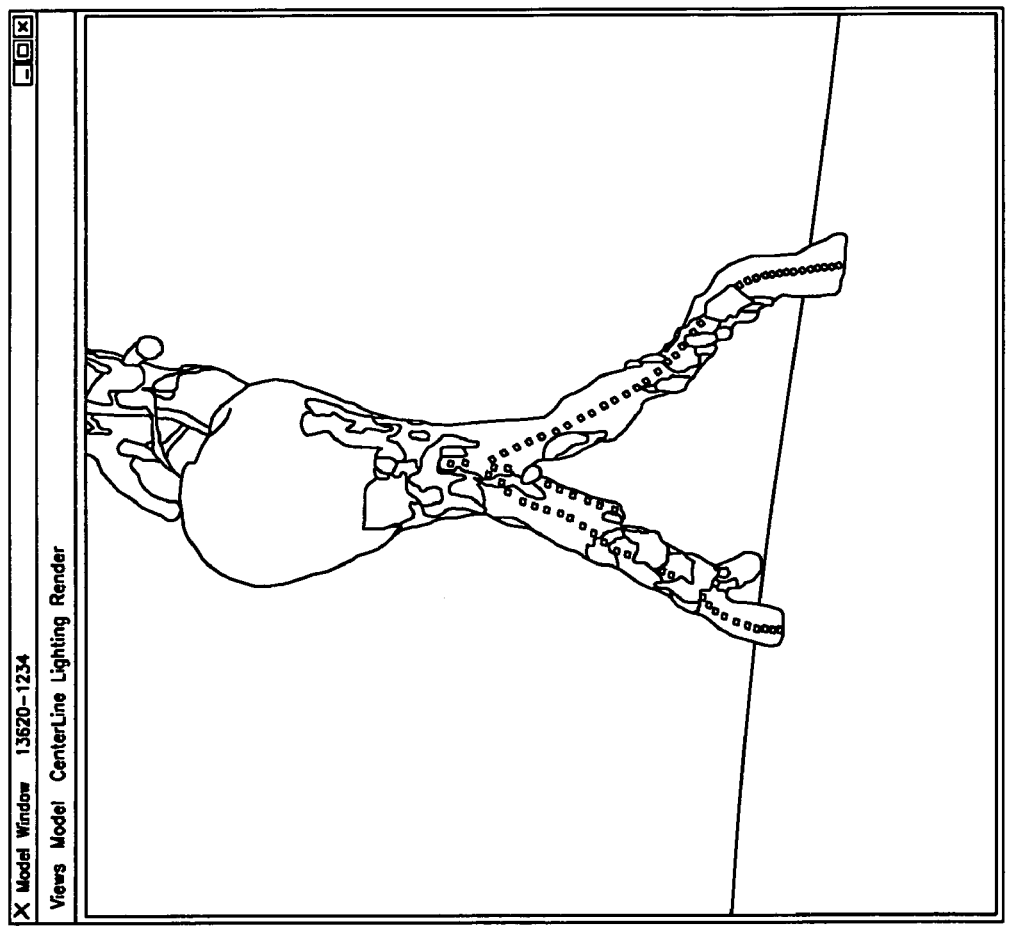
FIG. 36 illustrates a virtual model of an aortic aneurysm, with additional elements (e.g., centerlines) added to the model.

See FIG. 36.

(iv) FEM Mesh Construction

The FEM element that is preferably used for AAA stress analysis is a reduced integration three-node shell and can be easily represented as a triangle mesh. There are many ways to build the triangle mesh that represents the outside surface of the vessel from an input segmentation. By way of example but not limitation, one preferred form of the invention uses the following multi-step process to build the triangle mesh:

(i) Perform shape-based interpolation so that the pixel-to-millimeter conversion factor is similar in the x, y and z axes. This action helps ensure that the triangles are more equilaterally shaped.

(ii) Apply a low-pass filter to the segmentation and decimate the segmentation in the x, y directions. These steps help remove "jagged edges" and "stair step" artifacts in the mesh.

(iii) Tessellate the triangle mesh from the processed segmentation.

(iv) Scale the triangle mesh from voxel space to millimeter space.

(v) Apply the well known "laplacian smoothing" algorithm to the triangle mesh. This action further reduces stress artifacts in the simulation.

(vi) Remove some number of the "worst shaped" triangles (e.g., 5%).

(vii) Write the file for FEM analysis based on the resulting triangle mesh. Preferably the file is written using the Abaqus INP format; then the INP file can be used directly by the Abaqus solver to produce stress outputs.

(v) Stress Analysis Post-Processing and Visualization

The FEM process results in the generation of a vast amount of data.

While simply looking at the element having the highest stress can provide good results in many cases, the analysis of known "outliers" (i.e., cases of very high, or very low, levels of wall stress) has led to the discovery of new ways to look at the data to better differentiate rupture and non-rupture cases. In accordance with the present invention, a large number of different post-processing methods, of varying complexity, have been developed, in an effort to find the most robust way to determine rupture risk in a given model. It is anticipated that, in practice, only one method will typically be used to report the risk of rupture; however, the various methods were used to better understand the distributions of stresses that lead to rupture.

Basic Analysis

The basic output of the FEM process are 4 stress tensors calculated for each element of the triangle mesh at each blood pressure. These stress tensors can be processed to determine the "Max Principal Stress" for each element. It is also possible to look at the stress at multiple locations throughout the thickness of the mesh shell. In one preferred form of the invention, the stress is examined in the middle of the shell (SMID). For the purposes of the present invention, calculating this value for each element in the model, and taking the max, may be referred to as "Method A".

Nodal Results

The FEM process does not produce results directly at nodes; however, this is a standard way to view results. To this end, the values at nodes can be calculated using, for example, two different methods. Both methods essentially average all of the elements surrounding a node so as to produce more robust results through averaging out of potential high stress elemental values, which may be artifacts of the FEM process or the original CT data.

The first method is to simply average the maximum elemental values at each element surrounding a node. For the purposes of the present invention, this method may be referred to as "Method B".

The second way to calculate these nodal values is to average the tensors of the all of the surrounding elements and then perform the "Max Principal Stress" calculation on this averaged composite to get a result. This method approximates the method that the Abaqus Viewer software uses when it displays nodal results. For the purposes of the present invention, this method may be referred to as "Method C".

Discontinuity Aware Methods

The patient pool for the risk of rupture analysis falls into two categories: rupture cases and non-rupture, or elective surgery, cases. The basic hypothesis of the risk of rupture analysis is that patients with a known rupture can be distinguished from those in the elective group solely by knowing the patient's calculated wall stress.

During an analysis of "outliers" (known observations with high stresses and low stresses), it was found that there was a high correlation between the observation "outliers" and highly discontinuous distributions of stress. By looking at histograms of "outliers" and good results, it was determined that it would often be safe to discount some of the higher stresses in a model, particularly if they did not appear in close proximity to other high stresses. This has led to the development of a host of new methods designed to identify what appears to be "stress artifacts".

A first method, which for the purposes of the present invention may be referred to as "Method D", is an absolute discontinuity limit. Here discontinuity is defined as the maximum difference between an element's value and its neighboring elements' values. Thus, the process starts at the highest stressed element, calculates its discontinuity and compares that calculated discontinuity to the absolute discontinuity limit. If the calculated discontinuity is higher than the absolute discontinuity limit, the algorithm looks at the next highest element and so on, until it finds one with a calculated discontinuity lower than the absolute discontinuity limit. This method has been performed for a range of different absolute discontinuity limits (e.g., from approximately 0.5 to approximately 10 N/cm$^2$).

This method has also been run on nodal values, which is essentially the same algorithm, although it ends up processing a far larger group of results, because each node may have approximately 6-7 neighbors and each nodal value is calculated from a similar number of elements.

Another variation that may be used with this method is a slight change to the way discontinuity is calculated. A summary of some exemplary variations for implementing "Method D" is illustrated in Table 1 below. The "original" "Method D" is an attempt to be less strict with the application of the discontinuity limit by only filtering out elements that were below the value of the original element. The "new" "Method D" calculates discontinuity above and below, and thus does not take into account any elements which have a neighboring value larger or smaller by more than the specified limit.

TABLE 1

The 4 versions of "Method D"

| Method D (# from .5 to 10) | Positive/Negative discontinuity | Negative discontinuity only |
|---|---|---|
| Elemental | D# (new) | D# (original) |
| Nodal | DN# (new) | DN# (original) |

"Method E" is very similar to "Method D", except that the discontinuity limit is calculated based on the maximum stress of the aneurysm. This approach has the effect of calculating the discontinuity separately for each blood pressure and max stress. Thus an E10, at blood pressure 120, which had a max Method A value of 34, would act like an absolute discontinuity of 3.4 (i.e., it would have a "Method D" value of 3.4).

"Method F" is based on histograms of the stresses calculated for the different "outliers". Many of the "outliers" only have a few highly stressed elements when compared to rupture "outliers" and known "good analyses". Thus, it can be hypothesized that one can simply remove a small percentage of the highest stresses elements and not affect the majority of models as much as the "outliers" are affected, thus aiding differentiation. In one form of the present invention, this method is performed on percentages from 0.05% to 0.15%, which cropps from 10 to 100 elements.

"Method G" is a simple output of the discontinuity of the highest stressed element. This calculation is performed using the "Positive/Negative Discontinuity Method", although the results are necessarily identical to the "original" discontinuity method for this element.

"Method H" represents another form of the invention, and has been developed in an effort to counteract an effect which can occur when running the simulation at many different blood pressures. More particularly, by using the absolute limit (i.e., "Method D") approach, a stricter discontinuity limit is inherently enacted when calculating results at higher blood pressures. Most elements' stress appear to increase approximately linearly with regard to blood pressure. If all elements increase like this at higher blood pressures, larger discontinuities at higher blood pressures are to be expected. This conclusion is born out through analysis of "Method G" results. While "Method E" tries to counteract this effect by calculating a new discontinuity for each blood pressure based on the maximum stress, this has the undesirable effect of applying high limits to precisely some of the models that need to be corrected due to the presence of artifacts.

The solution of "Method H" is to calculate the number of elements "thrown away" for a particular discontinuity at the lowest blood pressure, and then to simply continue to "throw out" that many elements at the rest of the blood pressures. With this approach, what is really being sought is a determination of which elements are unacceptable due to artifacts or high discontinuities. This "throw away" set can be calculated once and then applied to all other blood pressures. In one embodiment of the present invention, it has been found acceptable to simply "remember" the number of elements to throw away. It is sometimes convenient to term this method the "SmartCrop" method because it acts as a simple crop of the top N elements, but this number is calculated in a model-specific way.

Another Method

"Method I" provides a different way to calculate the values at a node. "Method I" is very similar to "Method B", i.e., the "Element Average Nodal" method, with the singular difference being that it assigns the median of surrounding elemental stresses to the node, rather than the average.

Aggregate Methods

"Method J" has been developed in an attempt to increase the minimum recognizable feature size. Due to the inherent limits of CT imagery, the minimum feature size will often be a couple of millimeters in diameter. Since a typical mesh model is much smaller than this, stressed regions that are smaller than a couple of millimeters in diameter are possible. Given this fact, it may be more appropriate to find the highest stressed "patch" of nodes for a given model.

Using the connection information of the mesh, it is possible to find all nodes within a certain distance from a given node. However, simply finding the distance from the origin node to its neighbor may give erroneous results in tortuous areas because the distance along the surface can be significantly shorter than this. Instead, a graph may be created originating from the base node, which calculates the distance to each of its neighbors as the shortest path along the edges of the graph. All nodes within the specified distance may then be included in the "neighborhood", thus yielding a patch with an approximate radius of the limiting distance around a node.

The algorithm creates this neighborhood, for a given node and distance, and then either (i) averages all of the contained nodes together, or (ii) takes the median and applies this value to the node. The algorithm does this for each node in the model and returns the highest value.

Inasmuch as this algorithm is particularly processor-time-intensive, it has refined to only look at some top percentage of the nodes. For a subset of models, it was found that looking at the top 1% was sufficient to find the highest 6-millimeter radius patch on the aneurysm.

"Method L" is based on the hypothesis that aneurysms with a higher number of highly stressed elements will be more likely to rupture than aneurysms with a smaller number of stressed elements. "Method L" simply reports the number of elements with a stress above some value X. Thus, L45 will report the number of elements in a model with a ("Method A") stress above 45 at the given blood pressure.

"Method M" is based on a premise which is similar to the premise of "Method L", but it simply looks at the average of the top N % of elements. Thus, M1 would average the ("Method A") stress of the top 1% of the elements in the model.

Summary of Methods

The various methods may be summarized as follows:
"Method A": Max Elemental Stress
"Method B": Element Averaged Nodal
"Method C": Abaqus Nodal
"Method D": Absolute Discontinuity Limited
"Method E": Elemental with Percent Discontinuity Limit
"Method F": Elemental with elimination of top N %
"Method G": Discontinuity of maximum stressed element
"Method H": SmartCrop
"Method I": Median Element Nodal
"Method J": Area Averaging
"Method L": Number of Nodes Above X Stress
"Method M": Average of Top N %

(vi) Blood Pressure Interpolation

The two primary inputs to the FEM-based stress analysis system are (i) the aneurysm shape as defined by the 3D reconstruction of the merged vessel segmentation as described above, and (ii) the patient's blood pressure. It is widely accepted that higher blood pressures cause more loading within the vessel wall and are more likely to rupture as a result. Inasmuch as the finite element analysis for the meshes can take many minutes to complete, it is cumbersome to repeat the analysis for any given blood pressure that the patient may present with. Thus, it can be desirable to make the following simplification:

(i) The full analysis is computed for blood pressures from 80 mmHg to 200 mmHg in increments of 20 mmHg. This is a total of seven separate loading conditions and represents a realistic minimum and maximum range of blood pressures.

(ii) To obtain the maximum wall stress for any given blood pressure, an interpolation function has been developed with is based on the group of seven known max wall stress values. It has been discovered through regression analysis of several cases that a linear function fits the data very nicely.

(iii) This interpolation may be performed for all the methods of post-processing described above.

(vii) Visualization of Stress And Reporting of Risk of Rupture

In one preferred form of the invention, the calculated blood vessel wall stress can be visualized for the user by color coding the exterior of the mesh according to wall stress values. More particularly, in this form of the invention, the polygons defined between the nodes can be color coded to reflect the level stress on a particular polygon, e.g., red for highest stress values, yellow for intermediate stress values, and green for low stress values. Alternatively, or in addition to the foregoing, the intensity of the color mapped to the polygon can reflect the intensity of the stress imposed on that polygon, e.g., darker shades indicating higher levels of stress and lighter shades indicating lower levels of stress. Furthermore, the calculated levels of stress can be color coded on the mesh nodes and/or the mesh legs rather than on the surface of the polygon.

Furthermore, various techniques can be used to report the risk of rupture based on the foregoing stress level analysis. For example, in one form of the invention, the system can simply report the highest calculated stress value found anywhere on the structure as a single numeric value. Or, in another form of the invention, the system can simply report a calculated probability of rupture, e.g., 32% probability of rupture. Furthermore, if desired, this calculated probability of rupture can be visualized on the model by color coding the outer surface of the model according to the probability of rupture, e.g., red for highest probabilities of rupture, yellow for intermediate probabilities of rupture, and green for low probabilities of rupture. Alternatively, or in addition to the foregoing, the intensity of the color can reflect the probabilities of rupture, e.g., darker shades indicating higher probabilities of rupture and lighter shades indicating lower probabilities of rupture. Furthermore, the calculated probabilities of rupture can be color coded on the mesh nodes and/or the mesh legs rather than on the surface of the model.

In addition to the foregoing, the probability of rupture can be calculated considering a group or ensemble of nodes or polygons using statistical analysis or other means of analysis. In addition, the probability of rupture can also be reported as an equivalent diameter, the equivalent diameter being a common form of reporting familiar to the surgeon.

FURTHER MODIFICATIONS

It will be understood that many additional changes in the details, materials, steps and arrangements of parts, which have been herein described and illustrated in order to explain the nature of the invention, may be made by those skilled in the art within the principles and scope of the invention as expressed in the appended claims.

What is claimed is:

1. A method for determining the risk of rupture of a blood vessel using a set of 2-D slice images obtained by scanning the blood vessel, the method comprising:
   generating a mesh model of the blood vessel using the set of 2-D slice images, wherein the mesh model reflects tissue type at different locations along the blood vessel;
   conducting finite element stress analysis on the mesh model with the identified blood pressure to calculate the level of stress at different locations along the mesh model; and
   determining the risk of rupture of the blood vessel by analyzing the levels of stress calculated at different locations along the mesh model with respect to the tissue type to calculate and report probability of rupture of the blood vessel.

2. A method according to claim 1, wherein the calculated levels of stress at different locations on the mesh model are visualized on the mesh model.

3. A method according to claim 2, wherein the calculated levels of stress at different locations on the mesh model are visualized on the mesh model by color coding the polygons of the mesh.

4. A method according to claim 2, wherein the calculated levels of stress at different locations on the mesh model are visualized on the mesh model by color coding the nodes of the mesh.

5. A method according to claim 2, wherein the calculated levels of stress at different locations on the mesh model are visualized on the mesh model by color coding the legs of the mesh.

6. A method according to claim 1 wherein the risk of rupture is visualized on the mesh model by color coding the polygons of the mesh.

7. A method according to claim 1, wherein the risk of rupture is visualized on the mesh model by color coding the nodes of the mesh.

8. A method according to claim 1, wherein the risk of rupture is visualized on the mesh model by color coding the legs of the mesh.

9. A method according to claim 1, wherein the mesh model is generated using a segmentation technique.

10. A method according to claim 9, wherein the segmentation technique comprises identifying specific anatomical objects in each 2-D slice and aggregating the identified anatomical objects in each 2-D slice so as to create the mesh model.

11. A method according to claim 9, wherein the segmentation technique further comprises removal of extraneous anatomy from each 2-D slice before aggregating the identified anatomical objects in each 2-D slice so as to create the mesh model.

12. A method according to claim 9, wherein the blood vessel comprises the aorta, and further wherein the extraneous anatomy comprises visceral blood vessels.

13. A method according to claim 9, wherein the generation of the mesh model of the vessel further comprises limiting of boundary delineation of the mesh model before conducting finite element stress analysis.

14. A method according to claim 13, wherein the blood vessel comprises the aorta, and further wherein the upper boundary delineation of the mesh model is determined from the slice where the segmentation begins, and the lower boundary delineation of the mesh model is determined from the slice where the left and right iliac branches become vertically aligned.

15. A method according to claim 10, wherein generation of the mesh model comprises:
(i) performing shape-based interpolation so that the pixel-to-millimeter conversion factor is similar in the x, y and z axes, whereby to help ensure that the mesh polygons are more equilaterally shaped;
(ii) applying a low-pass filter to the segmentation and decimating the segmentation in the x, y directions, whereby to help remove jagged edges and stair step artifacts in the mesh;
(iii) tessellating the polygon mesh from the processed segmentation;
(iv) scaling the polygon mesh from voxel space to millimeter space;
(v) applying the laplacian smoothing algorithm to the polygon mesh, whereby to further reduce stress artifacts in the simulation;
(vi) removing a selected number of the worst shaped polygons; and
(vii) storing the mesh model in a format which may be used for finite stress analysis.

16. A method according to claim 15, wherein the mesh model is stored in Abaqus INP format.

17. A method according to claim 15, wherein the mesh model is stored in Abaqus INP format, and further wherein the INP file is input directly into the Abaqus solver to produce stress outputs.

18. A method according to claim 1, wherein the risk of rupture is determined at the mesh element having the highest stress.

19. A method according to claim 1, wherein the risk of rupture is determined by calculating the stress tensors for each element in the polygon mesh and taking the maximum of the same.

20. A method according to claim 1, wherein the risk of rupture is determined by calculating the stress level for each node in the polygon mesh and taking the maximum of the same.

21. A method according to claim 20, wherein the stress level for each node is calculated by averaging the maximal elemental values at each element surrounding the node.

22. A method according to claim 20, wherein the stress level for each node is calculated by averaging the tensors of all the surrounding elements and then performing the Max Principal Stress calculation on this average composite to get a result.

23. A method according to claim 1, wherein the risk of rupture is determined by: starting at the highest stressed element, calculating its discontinuity and comparing that calculated discontinuity to an absolute discontinuity limit; if the calculated discontinuity is higher than the absolute discontinuity limit, the process turns to the next highest element and so on, until the process finds one element with a calculated discontinuity lower than the absolute discontinuity limit.

24. A method according to claim 1, wherein the risk of rupture is determined by: starting at the highest stressed element, calculating its discontinuity and comparing that calculated discontinuity to a discontinuity limit that is calculated based on the maximum stress of the blood vessel; if the calculated discontinuity is higher than the absolute discontinuity limit, the process turns to the next highest element and so on, until the process finds one element with a calculated discontinuity lower than the absolute discontinuity limit.

25. A method according to claim 1, wherein the risk of rupture is determined by removing a small percentage of the highest stressed elements.

26. A method according to claim 1, wherein the risk of rupture is determined by using the discontinuity of the highest stressed element.

27. A method according to claim 1, wherein the risk of rupture is determined by discarding a selected number of elements based on discontinuity at a low blood pressure, and then discarding that same number of elements at higher blood pressures.

28. A method according to claim 20, wherein the stress level for each node is calculated by taking the median of the elemental values at each element surrounding the node.

29. A method according to claim 1, wherein the risk of rupture is determined by finding the highest stressed group of nodes for a given model.

30. A method according to claim 1, wherein the risk of rupture is determined by identifying the number of elements with a stress level above some predetermined value.

31. A method according to claim 1, wherein the risk of rupture is determined by identifying the average of the top N % of elements.

32. A method according to claim 1, wherein the levels of stress are first calculated for a plurality of pre-determined blood pressures, and then the wall stress for a patient's actual measured blood pressure is determined by interpolating from the wall stresses calculated from the plurality of pre-determined blood pressures.

33. A method according to claim 1, wherein the levels of stress are (i) first calculated for a plurality of pre-determined blood pressures, and (ii) thereafter calculated for a patient's actual measured blood pressure, and further wherein the level of stress is calculated for the patient's actual measured blood pressure by interpolating from the wall stresses previously calculated from the plurality of pre-determined blood pressures.

34. A system for determining the risk of rupture of a blood vessel using a appropriate set of 2-D slice images obtained by scanning the blood vessel, the system configured to perform the steps of:
generating a mesh model of the blood vessel using the set of 2-D slice images, wherein the mesh model reflects tissue type at different locations along the blood vessel;
conducting finite element stress analysis on the mesh model with the identified blood pressure to calculate the level of stress at different locations along the mesh model; and
determining the risk of rupture of the blood vessel by analyzing the levels of stress calculated at different locations along the mesh model with respect to the tissue type to calculate and report probability of rupture of the blood vessel.

* * * * *